(12) United States Patent  (10) Patent No.: US 7,078,168 B2
Sylvan  (45) Date of Patent: Jul. 18, 2006

(54) METHOD FOR DETERMINING ALLELE FREQUENCIES

(75) Inventor: Anna Sylvan, Uppsala (SE)

(73) Assignee: Biotage AB, Uppsala (SE)

( * ) Notice: Subject to any disclaimer, the term of this patent is extended or adjusted under 35 U.S.C. 154(b) by 0 days.

(21) Appl. No.: 10/085,774

(22) Filed: Feb. 27, 2002

(65) Prior Publication Data
US 2003/0082566 A1 May 1, 2003

Related U.S. Application Data

(60) Provisional application No. 60/271,703, filed on Feb. 27, 2001.

(51) Int. Cl.
C07H 21/04 (2006.01)
C12Q 1/68 (2006.01)

(52) U.S. Cl. .................. 435/6; 435/91.1; 435/91.2; 536/23.1; 536/24.3

(58) Field of Classification Search .............. 435/6, 435/91.2, 91.1, 174; 536/23.1, 24.3
See application file for complete search history.

(56) References Cited

U.S. PATENT DOCUMENTS 6,020,137 A * 2/2000 Lapidus et al. ............. 435/6
6,287,778 B1 * 9/2001 Huang et al. ............... 435/6
6,566,101 B1 * 5/2003 Shuber et al. ............ 435/91.2
6,750,018 B1 * 6/2004 Kambara et al. ............. 435/6

FOREIGN PATENT DOCUMENTS

WO    WO 9828440 A1 * 7/1998

OTHER PUBLICATIONS

Nyren et al. "Detection of Single-Base changes using a bioluminometric primer extension assay." Analytical Biochemistry. Vo 244, pp. 367-373, 1997.*
Breen et al. "Determining SNP allele frequencies in DNA pools." BioTechniques. vol. 28, No. 3, pp. 464-470, Mar. 2000.*
Arnheim, N. et al. 1985. *Proc. Natl. Acad. Sci.* 82: 6970-6974.
Breen, G. et al. 1999. *Mol Cell Probes* 13(5): 359-365.
Breen, G. et al. 2000. *Biotechniques* 28(3): 464-3, 470.
Collins, H.E. et al. 2000. *Hum. Genet.* 106(2): 218-26.
Germer, S. et al. 2000. *Genome Res.* 10(2): 258-266.
Kruglyak, L. 1999. *Nat. Genet.* 22: 139-144.
Kwok, P. et al. 1994. *Genomics* 23: 138-144.
Pacek, P. et al. 1993. *PCR Methods Applic.* 2: 313-317.
Risch, N. and Merikangas, K. 1996. *Science* 273: 1516-1517.
Risch, N. and Teng, J. 1998. *Genome Res.* 8: 1273-1288.
Shaw, S. H. et al. 1998. *Genome Res.* 8: 111-123.
Bellman et al. 2000. Poster entitled "Reliable SNP assessment and allele frequency determination by Pyrosequencing" presented Apr. 9, 2000 at Human Genome Project Meeting, Vancouver.
Ekstrom. 2000. Printed copy of presentation slides and conference program for talk given Feb. 27, 2000 at Genomic Opportunities Conference, San Francisco.

* cited by examiner

*Primary Examiner*—Jeanine A. Goldberg
(74) *Attorney, Agent, or Firm*—Dorsey & Whitney LLP

(57) ABSTRACT

The present invention related to a method of determining the frequency of an allele in a population of nucleic acid molecules. The method comprises pooling the nucleic acid molecules of a population of nucleic acids, performing primer extension reactions using a primer which binds at a predetermined site located in nucleic acid molecules, and obtaining a pattern of nucleotide incorporation.

16 Claims, 16 Drawing Sheets nucleotide incorporated nucleotide incorporated

SEQUENCE LISTING

<160> NUMBER OF SEQ ID NOS: 40

<210> SEQ ID NO 1
<211> LENGTH: 12
<212> TYPE: DNA
<213> ORGANISM: Homo sapiens
<220> FEATURE:
<221> NAME/KEY: misc_feature
<222> LOCATION: ()..()
<223> OTHER INFORMATION: n can be c, t or g

<400> SEQUENCE: 1
naaggttgtc ct                                                          12

<210> SEQ ID NO 2
<211> LENGTH: 10
<212> TYPE: DNA
<213> ORGANISM: Homo sapiens
<220> FEATURE:
<221> NAME/KEY: misc_feature
<222> LOCATION: ()..()
<223> OTHER INFORMATION: n is c or t

<400> SEQUENCE: 2 ngttccacct                                                             10

<210> SEQ ID NO 3
<211> LENGTH: 17
<212> TYPE: DNA
<213> ORGANISM: artificial sequence
<220> FEATURE:
<221> NAME/KEY: misc_feature
<222> LOCATION: ()..()
<223> OTHER INFORMATION: Primer - E1a

<400> SEQUENCE: 3
ggtcgggctg ggaagat                                                17

<210> SEQ ID NO 4
<211> LENGTH: 17
<212> TYPE: DNA
<213> ORGANISM: artificial sequence
<220> FEATURE:
<221> NAME/KEY: misc_feature
<222> LOCATION: ()..()
<223> OTHER INFORMATION: Primer -E1b

<400> SEQUENCE: 4
gctcccgcag aggaagc                                                17

<210> SEQ ID NO 5
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: Primer - E1s

<400> SEQUENCE: 5
agaaagggcc tcctctcttt                                             20

<210> SEQ ID NO 6
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: Primer - E4a

<400> SEQUENCE: 6
gccaggaagt ttgatgtgaa c                                           21

<210> SEQ ID NO 7
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: Primer - E4b

<400> SEQUENCE: 7
gattcccctc tccctgtacc t                                           21

<210> SEQ ID NO 8
<211> LENGTH: 17
<212> TYPE: DNA
<213> ORGANISM: artificial sequence
<220> FEATURE:
<221> NAME/KEY: misc_feature
<222> LOCATION: ()..()

```
<223> OTHER INFORMATION: Primer - E4s

<400> SEQUENCE: 8
gacctagaac gggcagc                                                  17

<210> SEQ ID NO 9
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: Primer - E7a

<400> SEQUENCE: 9
tgatgtaacc ctcctctcca                                               20

<210> SEQ ID NO 10
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: Primer - E7b

<400> SEQUENCE: 10
cggcttacct tctgctgtag t                                             21

<210> SEQ ID NO 11
<211> LENGTH: 17
<212> TYPE: DNA
<213> ORGANISM: artificial sequence
<220> FEATURE:
<221> NAME/KEY: misc_feature
<222> LOCATION: ()..()
<223> OTHER INFORMATION: Primer - E7s

<400> SEQUENCE: 11
acggcagctt cttcccc                                                  17

<210> SEQ ID NO 12
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 145

<400> SEQUENCE: 12
ggctgctgtt ctgaaaccat ctga                                          24

<210> SEQ ID NO 13
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 146

<400> SEQUENCE: 13
ttcaggaacg cgggcaagtc                                               20

<210> SEQ ID NO 14
<211> LENGTH: 15
```

```
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 147

<400> SEQUENCE: 14
gagcagtccc caccc                                              15

<210> SEQ ID NO 15
<211> LENGTH: 15
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 148

<400> SEQUENCE: 15
gcgggcaagt ccaat                                              15

<210> SEQ ID NO 16
<211> LENGTH: 23
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 149

<400> SEQUENCE: 16
ggaacactgc ctcccacttt ctt                                     23

<210> SEQ ID NO 17
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 150

<400> SEQUENCE: 17
tccccatgca gccctagaga c                                       21

<210> SEQ ID NO 18
<211> LENGTH: 17
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 151

<400> SEQUENCE: 18
ggagaagtcc agtgtgc                                            17

<210> SEQ ID NO 19
<211> LENGTH: 21
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 182

<400> SEQUENCE: 19
```

```
ttccaaagga cgcgaccata a                                                21

<210> SEQ ID NO 20
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 183

<400> SEQUENCE: 20
cctgcacccc agaccactga                                                  20

<210> SEQ ID NO 21
<211> LENGTH: 14
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 184

<400> SEQUENCE: 21
tagctgcgcg ggaa                                                        14

<210> SEQ ID NO 22
<211> LENGTH: 18
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 155

<400> SEQUENCE: 22
cctacccaca ggccagaa                                                    18

<210> SEQ ID NO 23
<211> LENGTH: 18
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 156

<400> SEQUENCE: 23
gcctgggacc tcactgtc                                                    18

<210> SEQ ID NO 24
<211> LENGTH: 17
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 157

<400> SEQUENCE: 24
ggagacagaa tgctgat                                                     17

<210> SEQ ID NO 25
<211> LENGTH: 20
<212> TYPE: DNA
<213> ORGANISM: artificial sequence
<220> FEATURE:
<221> NAME/KEY: misc_feature
```

-continued

```
<222> LOCATION: ()..()
<223> OTHER INFORMATION: Primer - PSO 158

<400> SEQUENCE: 25
gttgccctct ggttccacct                                              20

<210> SEQ ID NO 26
<211> LENGTH: 22
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 159

<400> SEQUENCE: 26
tgtctccagc agctccttca tc                                           22

<210> SEQ ID NO 27
<211> LENGTH: 14
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 160

<400> SEQUENCE: 27
gcccaggaag gaac                                                    14

<210> SEQ ID NO 28
<211> LENGTH: 23
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 167

<400> SEQUENCE: 28
gatgctgtaa cagagacccc ata                                          23

<210> SEQ ID NO 29
<211> LENGTH: 23
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 168

<400> SEQUENCE: 29
ctgggattac aggtgtgaac act                                          23

<210> SEQ ID NO 30
<211> LENGTH: 18
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 169

<400> SEQUENCE: 30
taggagcaag aagtaaac                                                18

<210> SEQ ID NO 31
```

```
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 173

<400> SEQUENCE: 31
caaggtagag aagtgcagca ttca                                          24

<210> SEQ ID NO 32
<211> LENGTH: 24
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 174

<400> SEQUENCE: 32
ttgattctct ttgagcccag atgt                                          24

<210> SEQ ID NO 33
<211> LENGTH: 16
<212> TYPE: DNA
<213> ORGANISM: artificial sequence
<220> FEATURE:
<221> NAME/KEY: misc_feature
<222> LOCATION: ()..()
<223> OTHER INFORMATION: Primer - PSO 175

<400> SEQUENCE: 33
gcctggagct gttaat                                                   16

<210> SEQ ID NO 34
<211> LENGTH: 38
<212> TYPE: DNA
<213> ORGANISM: artificial sequence
<220> FEATURE:
<221> NAME/KEY: misc_feature
<222> LOCATION: ()..()
<223> OTHER INFORMATION: oligonucleotide - PSO43SNP

<400> SEQUENCE: 34
agtcatggtg ctggggcact ggccgtcgtt ttacaacg                           38

<210> SEQ ID NO 35
<211> LENGTH: 38
<212> TYPE: DNA
<213> ORGANISM: artificial sequence
<220> FEATURE:
<221> NAME/KEY: misc_feature
<222> LOCATION: ()..()
<223> OTHER INFORMATION: oligonucleotide - PSO44SNP

<400> SEQUENCE: 35
agtcatggtg ctagggcact ggccgtcgtt ttacaacg                           38

<210> SEQ ID NO 36
<211> LENGTH: 39
<212> TYPE: DNA
<213> ORGANISM: artificial sequence
<220> FEATURE:
<221> NAME/KEY: misc_feature
<222> LOCATION: ()..()
<223> OTHER INFORMATION: oligonucleotide - PSO44SNP

<400> SEQUENCE: 36
```

```
agtcatggtg ctgggggcac tggccgtcgt tttacaacg                               39

<210> SEQ ID NO 37
<211> LENGTH: 39
<212> TYPE: DNA
<213> ORGANISM: artificial sequence
<220> FEATURE:
<221> NAME/KEY: misc_feature
<222> LOCATION: ()..()
<223> OTHER INFORMATION: oligonucleotide - PSO45SNP

<400> SEQUENCE: 37
agtcatggtg ctagggcac tggccgtcgt tttacaacg                                39

<210> SEQ ID NO 38
<211> LENGTH: 41
<212> TYPE: DNA
<213> ORGANISM: artificial sequence
<220> FEATURE:
<221> NAME/KEY: misc_feature
<222> LOCATION: ()..()
<223> OTHER INFORMATION: oligonucleotide - PSO53SNP

<400> SEQUENCE: 38
agtcatggtg ctaaggggc actggccgtc gttttacaac g                             41

<210> SEQ ID NO 39
<211> LENGTH: 41
<212> TYPE: DNA
<213> ORGANISM: artificial sequence
<220> FEATURE:
<221> NAME/KEY: misc_feature
<222> LOCATION: ()..()
<223> OTHER INFORMATION: oligonucleotide - PSO54SNP

<400> SEQUENCE: 39
agtcatggtg ctaaaggggc actggccgtc gttttacaac g                            41

<210> SEQ ID NO 40
<211> LENGTH: 17
<212> TYPE: DNA
<213> ORGANISM: artificial sequence
<220> FEATURE:
<221> NAME/KEY: misc_feature
<222> LOCATION: ()..()
<223> OTHER INFORMATION: Primer- PSO55NUSPT

<400> SEQUENCE: 40
cgttgtaaaa cgacggc                                                       17
```

METHOD FOR DETERMINING ALLELE FREQUENCIES

CROSS-REFERENCE TO RELATED APPLICATION

This application claims the benefit of U.S. application Ser. No. 60/271,703 filed Feb. 27, 2001, the disclosure of which is incorporated herein by reference.

BACKGROUND OF THE INVENTION

The invention relates to a method of determining the frequency of an allele within a given population or group, and in particular to a method of determining allele frequencies for single nucleotide polymorphisms (SNPs) or other mutations or genetic variations (e.g. nucleotide insertions, additions or deletions, gene, chromosome or genome duplications (or multiplications) etc. in pooled nucleic acid samples or other samples (including single samples) which may contain allelic variants.

Individuals in populations will have genetic differences. The genetic differences may be represented as the individuals in the population having different alleles at a given locus. Alternatively genetic differences can be related to gene, chromosome, or whole genome duplications (or other multiplications). The allele frequency describes the fraction of the population exhibiting a particular allele. Over a whole population, there may be many different alleles at a particular locus. However, where the genetic difference occurs as alterations of a single nucleotide (single nucleotide polymorphisms or SNPs), generally only 2 alleles are present in the population, although triallelic or tetrallelic SNPs are known. Studies of allelic association in populations are one of the most useful and powerful methods for mapping genes/mutations that contribute to disease. Such studies require the determination of the genotype (i.e. which allele is present) at one or several loci in a population. The frequency of a particular allele in a given population can be assessed, and the association of that allele with a disease or other clinical condition (e.g. predisposition to disease, therapeutic responsibility etc.) can be studied.

Single nucleotide polymorphisms (SNPs) are regularly used for genetic association studies, and consist of single nucleotide substitutions. SNPs are normally biallelic markers (i.e. there are 2 alleles present in the population), and are the markers of choice for various types of genetic analysis, because of their high frequency in the genome. SNPs are found approximately once every 100 to 1000 bases in the human genome. An SNP has a prevalence of at least 1% in a given population. Further, they are stable, having much lower mutation rates than repeat sequences, for example. The analysis of SNPs is of great importance in several disciplines within the applied genomic field. Importantly, the nucleotide sequence variations that are most likely to be responsible for the functional changes of interest will be SNPs. Such variations are therefore of great interest, and many studies directed to identify functional SNPs contributing to (or associated with) a particular trait or disease ("phenotype") have been performed. Thus many diseases and conditions may be associated with (or linked to) single nucleotide polymorphisms, either alone or in combination. For example, in WO 00/22166, it has been suggested that a combination of SNPs within several genes gives a polymorphic pattern which may be used to predict the likelihood of developing cardiovascular disease. Obtaining reliable and accurate data on the frequencies of a given SNP allele in a given population without testing each member of the population would have a revolutionary impact on the efficiency and cost of analysis for large population studies.

However, the frequency of other genetic mutations or variants, e.g. insertion/addition/deletion mutations and gene, chromosome or genome duplications (in the sense of any number of multiplications or repeats), and those studied in cancer genetics and chromosomal abnormality (e.g. trisomy) cases, can be analysed by the method of the invention.

Allelic association means that across a given population, individuals who have a certain allele at one locus may have a statistically higher chance of developing a particular disease, for example. Thus, the possession of a particular allele can cause direct susceptibility to a disease. Alternatively, the possession of a particular allele may be indirectly linked to disease susceptibility via association with the "disease" allele.

Association studies attempt to find genes that influence or increase susceptibility to disease or traits in any organism. This involves determining the frequency of an allele from a population of organisms with that trait or disease and comparing the results with a control population that do not exhibit the disease or trait. Various statistical/mathematical methods are known and described in the art for assessing allele frequencies based on such studies. In order to perform large-scale association studies for single nucleotide polymorphisms, methods have included labourious and expensive individual genotyping of individual nucleic acid samples. Pooling of nucleic acid samples in order to obtain allele frequency information has been used to reduce the burden of genotyping individual samples. To date, most pooling investigations have centred on the use of microsatellite polymorphisms, with few methods developed for the rapid assessment of SNPs in a given population.

Studies on allele frequencies tend to rely on radiation-based methods, or gel electrophoresis, which have well-known drawbacks. A method of determining SNP allele frequency using allele-specific fluorescent probes in the Taqman® assay (Breen et al., Biotechniques 2000, 28(3) 464–470) has been developed by PE Biosystems. In this technique Taqman® probes are used to detect specific sequences in Polymerase Chain Reaction (PCR) products by employing the 5' 3' exonuclease activity of Taq polymerase. The Taqman® probe anneals to the target sequence between the traditional forward and reverse PCR primers. The Taqman® probe is labelled with a reporter fluorophore and a quencher fluorochrome. This technique relies on the possibility of designing allele specific probes that match the annealing temperature of the PCR primers. Moreover, the allele specificity of the probe is, in the case of SNPs, determined by one out of 17–30 bases. These restrictions make it hard to design allele specific probes showing good enough temperature discrimination not to bind to the other allele. Hence, the signal from such an assay might not always accurately represent the frequency of the probe specific allele. A disadvantage of this method may be in finding assay conditions where a mismatch results in clearly distinguishable difference in cleavage of the reporter fluorophore on the two alleles. Further, Taqman® probes have different dyes at the 5' and 3' ends and are therefore costly to produce, and must be carefully designed. Taqman requires two reactions in order to measure allele frequency, using a different probe in each of the two reactions, complementary to either allele. It would therefore be advantageous to develop a method of determining SNP allele frequencies in pooled nucleic acid in one reaction which was accurate, reliable and that avoided the need for labels or relied on probe binding to the SNP site.

BRIEF SUMMARY OF THE INVENTION

It has now been found that a simple, reliable, reproducible and accurate method for determining the frequency of an allele in a given population, may be performed by pooling the nucleic acid sequences of the said population and performing a "primer-extension" type reaction, using primers designed for particular SNPs/alleles, and detecting the pattern of incorporation of nucleotides in said "primer-extension" reaction. The pattern may then be analysed to determine the frequency of each allele in the pooled nucleic acid.

The method is particularly suited to automation e.g. in systems where reaction and reagent dispensing steps take place in a microtitre plate format. The methods are particularly suited for finding SNP markers that are correlated to a certain trait, for example a specific disease, but may also find application in other allele frequency applications, such as SNP confirmation or analysis of mutations associated with cancer or chromosome abnormalities, especially abnormalities of chromosome number, and other mutations or variations involving duplication or loss of chromosomes or genes.

As described further below the present invention is advantageously based on a method of "sequencing-by-synthesis" (see e.g. U.S. Pat. No. 4,863,849 of Melamede). This is a term used in the art to define sequencing methods which rely on the detection of nucleotide incorporation during a primer-directed polymerase extension reaction. The four different nucleotides (i.e. A, G, T or C nucleotides) are added cyclically or sequentially (conveniently in known order), and the event of incorporation can be detected directly or indirectly. This detection reveals which nucleotide has been incorporated, and hence sequence information, when the nucleotide (base) which forms a pair (according to the normal rules of base pairing, A-T and C-G) with the next base in the template sequence is added, it will be incorporated into the growing complementary strand (i.e. the extended primer) by the polymerase, and this incorporation will trigger a detectable signal, the nature of which depends upon the detection strategy selected.

96 system instrument using Pyrosequencing™ SNP reagent kit. The peak heights were measured in order to calculate the frequency of the allele. The results are shown generally as nucleotide incorporated (i.e. A, C, G or T) versus amount of light released (in RLU). The 2 nucleotide incorporations which relate to the SNP are marked. The experimental conditions are as described in Example 4.

Figure 4A:
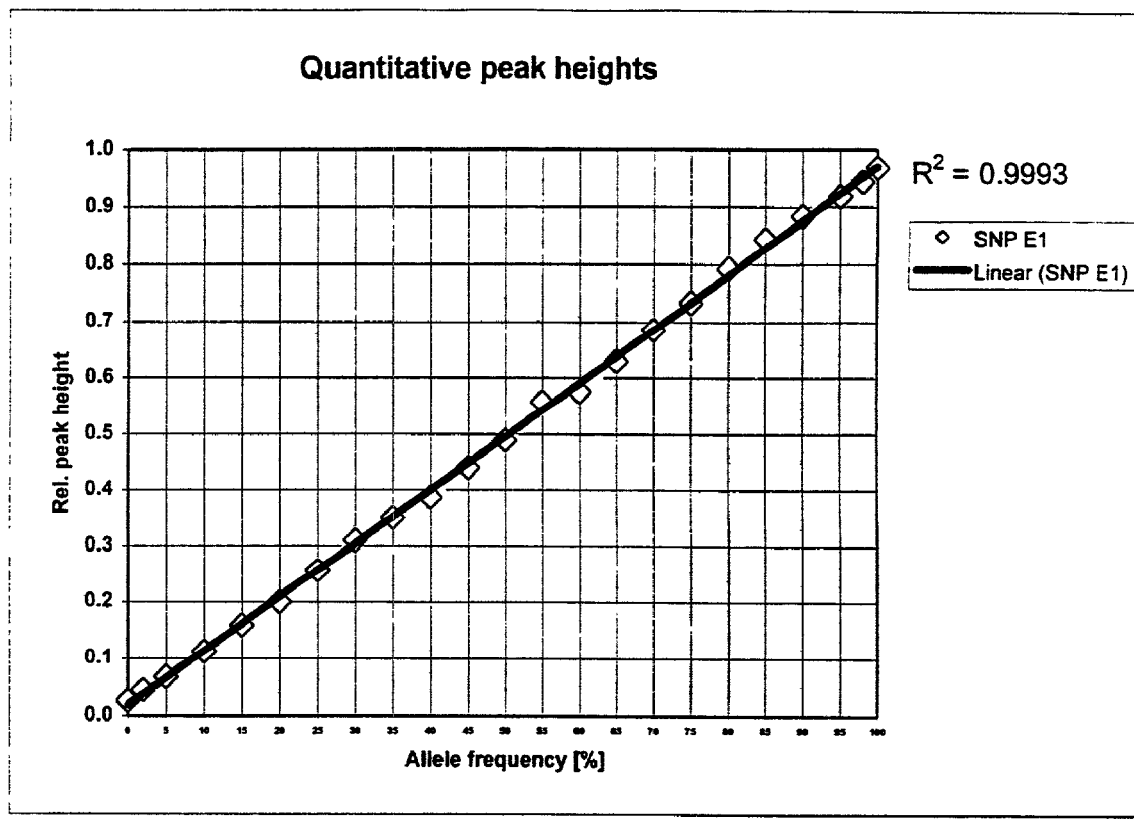

FIG. 4a depicts graphically relative peak heights from a Pyrosequencing reaction plotted against allele frequency. The SNP analysed was SNPE1. 5 pmol pooled DNA PCR product was incubated with 17.5 µl magnetic beads, and Pyrosequencing™ was performed using the primer as shown in Example 1. The resulting peak heights were plotted versus expected allele frequency, and a linear relationship between the 2 was demonstrated. The experimental conditions are as set out in Example 5.

Figure 4B:
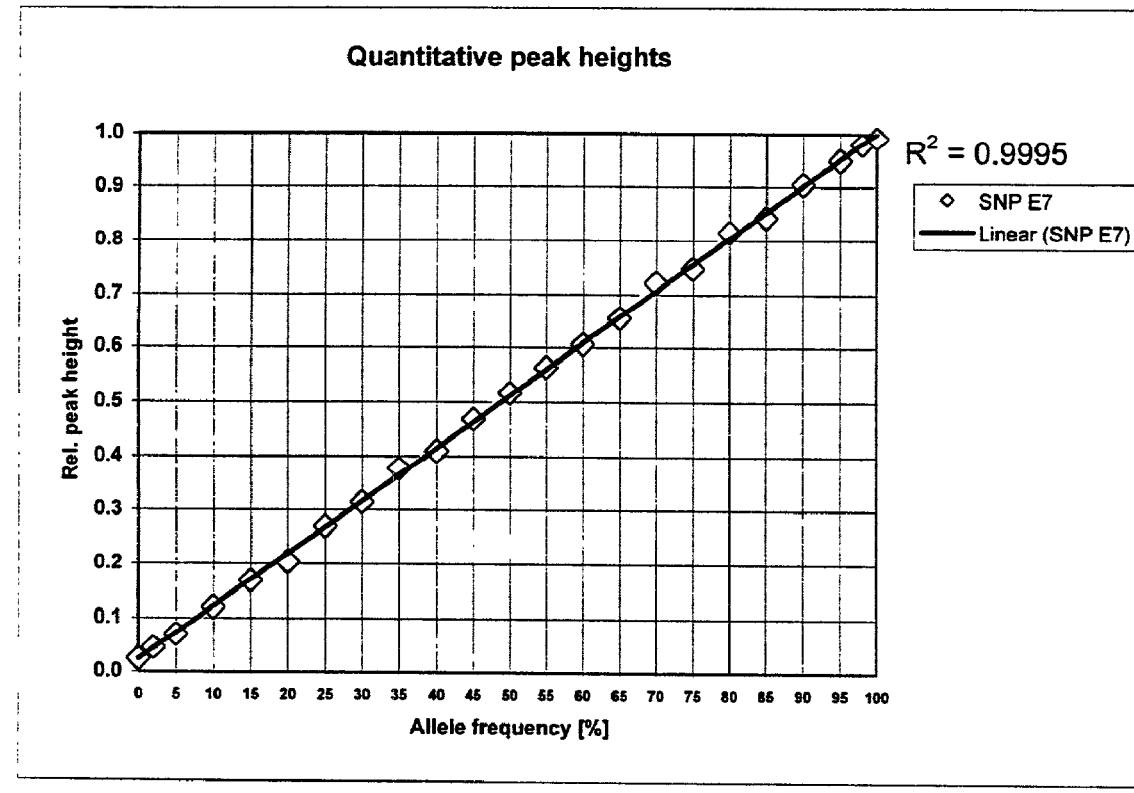

FIG. 4b depicts graphically relative peak heights from a Pyrosequencing reaction plotted against allele frequency. The SNP analysed was SNPE7. 5 pmol pooled DNA PCR product was incubated with 17.5 µl magnetic beads, and Pyrosequencing™ was performed using the primer as shown in Example 1. The resulting peak heights were plotted versus expected allele frequency, and a linear relationship between the 2 was demonstrated. The experimental conditions are as set out in Example 5.

Figure 4C:
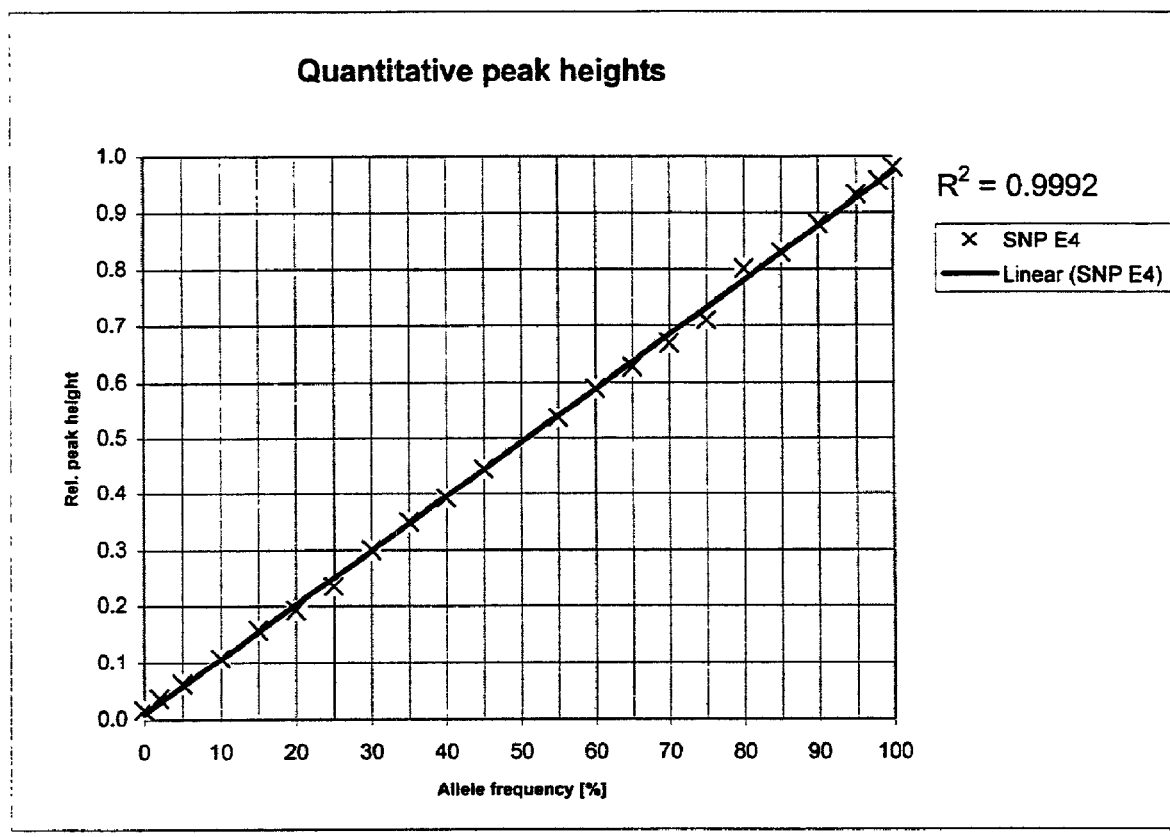

FIG. 4c depicts graphically relative peak heights from a Pyrosequencing reaction plotted against allele frequency. The SNP analysed was SNPE4. 5 pmol pooled DNA PCR product was incubated with 17.5 µl magnetic beads, and Pyrosequencing™ was performed using the primer as shown in Example 1. The resulting peak heights were plotted versus expected allele frequency, and a linear relationship between the 2 was demonstrated. The experimental conditions are as set out in Example 5.

Figure 5:
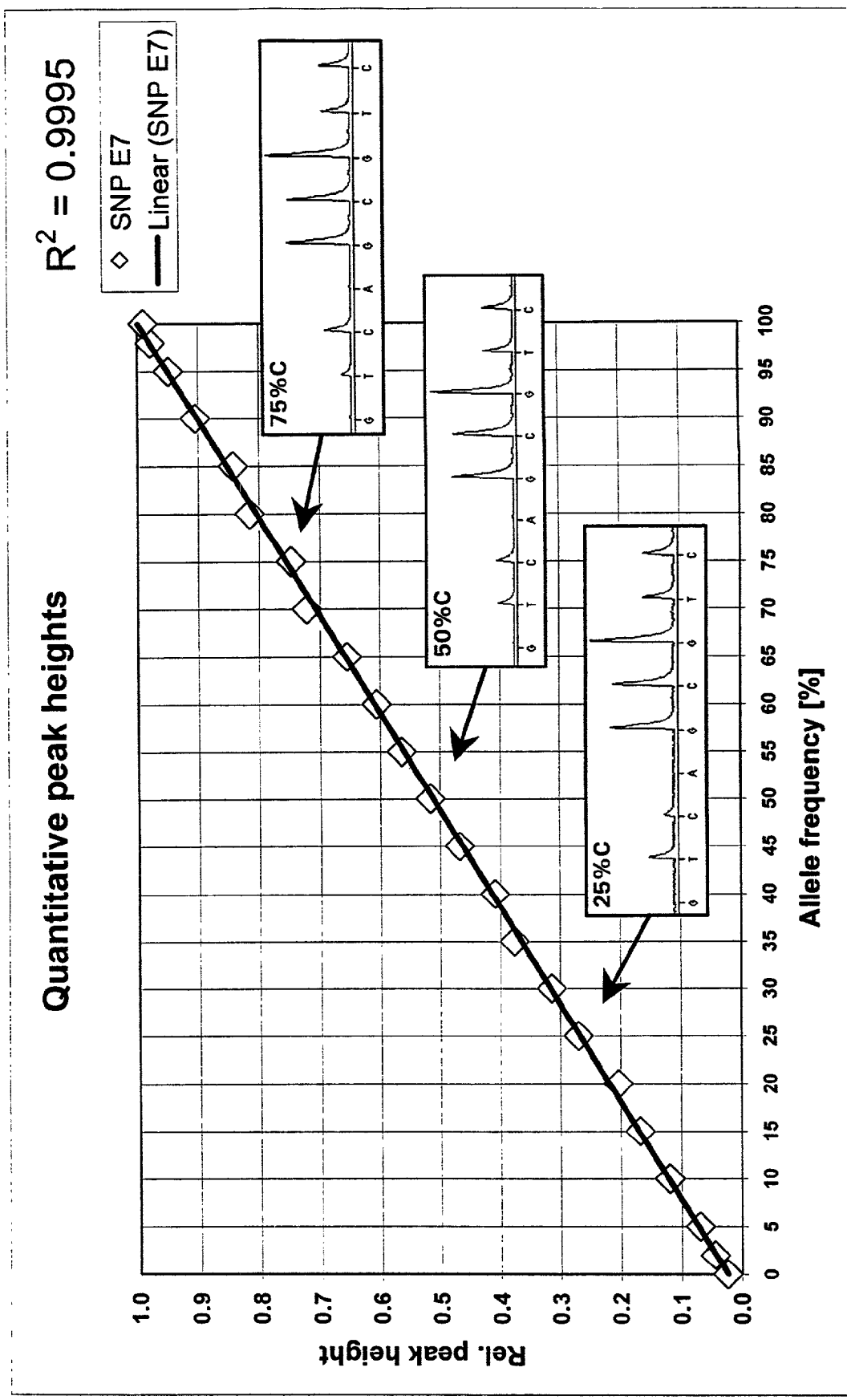

FIG. 5 is a further representation of FIG. 4b. Also depicted on this figure are the Pyrogram™ plots showing 25% C, 50% C and 75% C peaks, which are correlated to points on the linear plot. Experimental conditions are described in Example 5.

Figure 6:
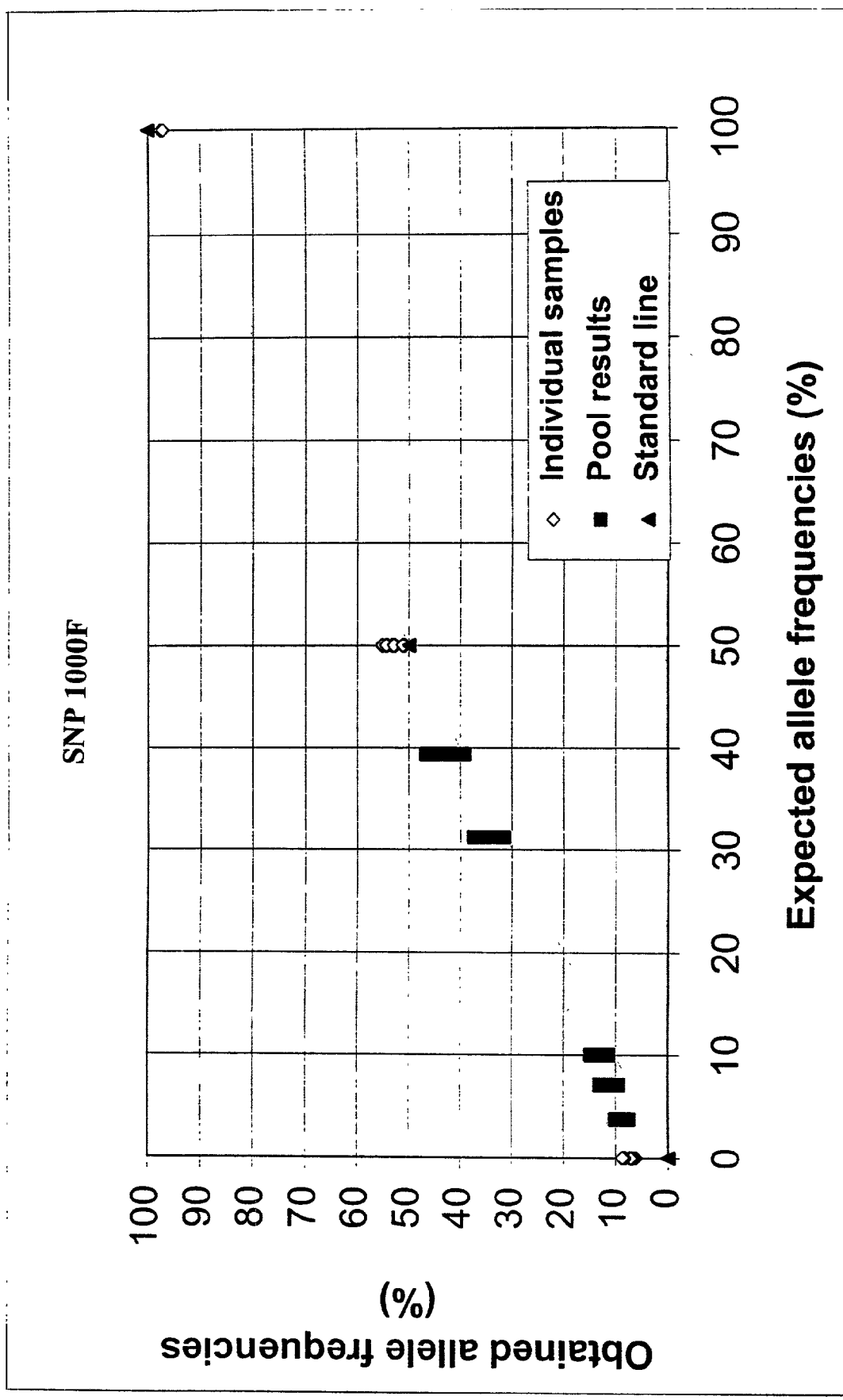

FIG. 6 depicts the obtained allele frequency results from Pyrosequencing™ for SNP 1000F and the expected allele frequency for the sample. The results are plotted as obtained allele frequency (%) versus expected allele frequencies (%). The standard line shows an imaginary pattern for an "ideal" SNP. 30 µl of PCR product was used for Pyrosequencing™, as described in Example 5.

Figure 7:
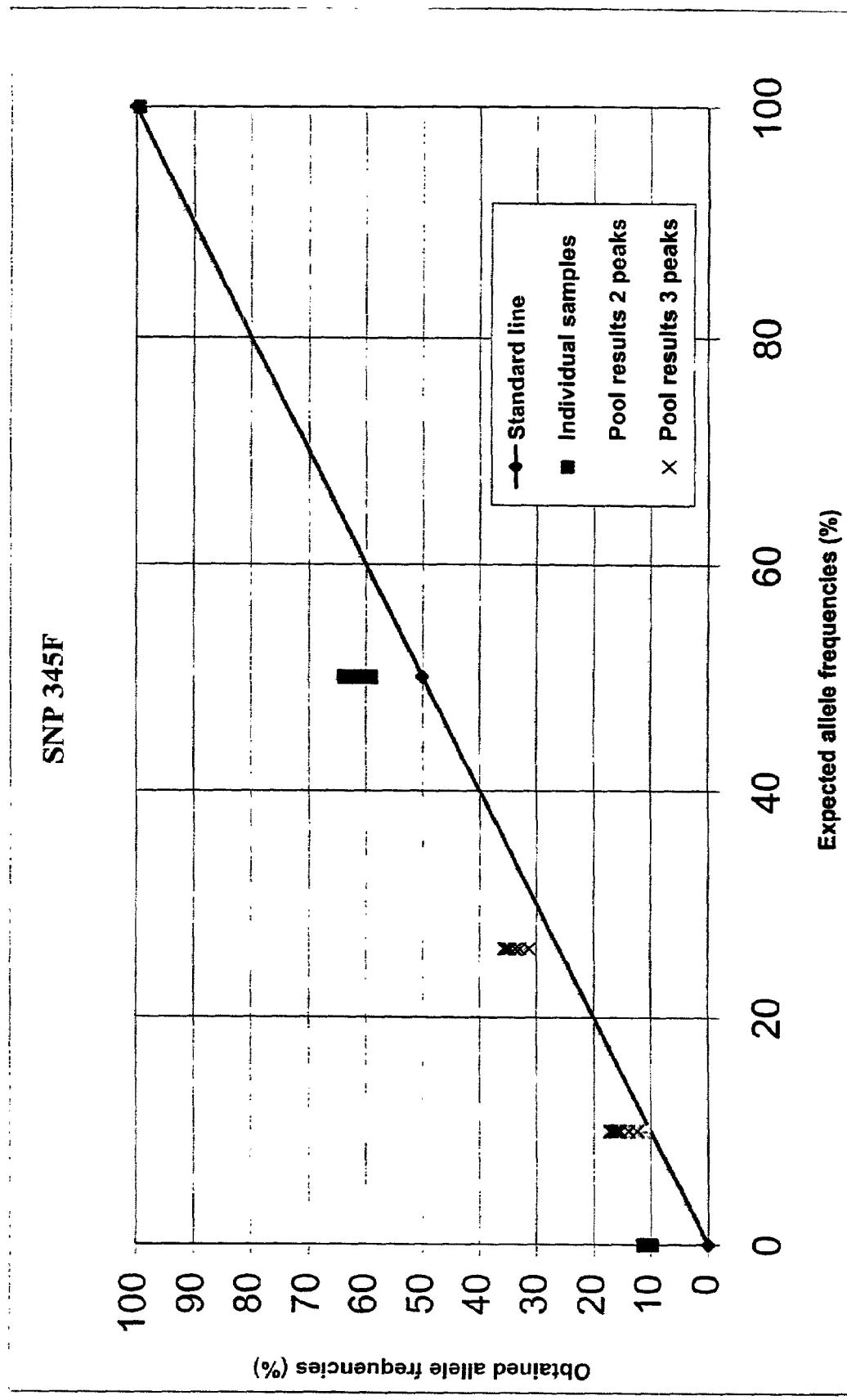

FIG. 7 depicts the obtained allele frequency results from Pyrosequencing™ for SNP 345F and the expected allele frequency for the sample. The results are plotted as obtained allele frequency (%) versus expected allele frequencies (%). The standard line shows an imaginary pattern for an "ideal" SNP. 30 µl of PCR product was used for Pyrosequencing™, as described in Example 5. Two pools were made, with expected allele frequencies of 10% A and 26% A.

Figure 8A:
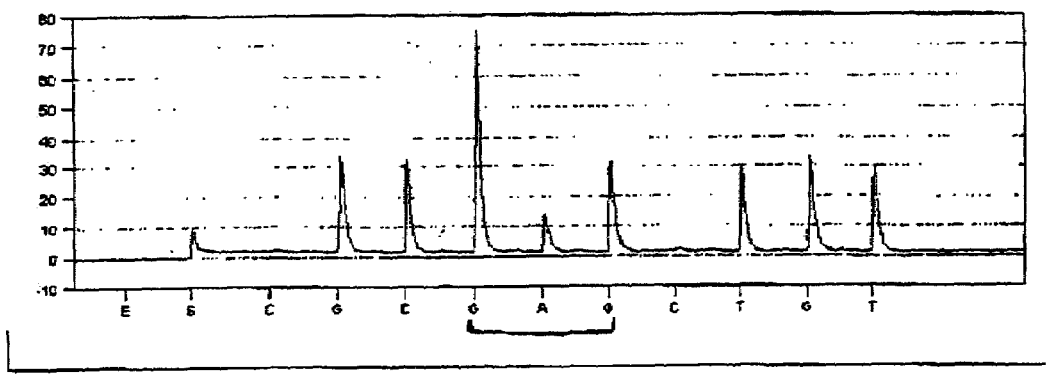

FIG. 8a shows DNA sequencing on pooled genomic DNA over SNP 345F (A/GGGG). 30 µl of PCR product was incubated with 10 µl magnetic beads and 20 µl of 2×BW buffer. Pyrosequencing™ was then performed on a PSQ™96 system instrument using Pyrosequencing™ SNP reagent kit. The resultant emitted light caused by nucleotide incorporation was measured and plotted as nucleotide incorporation V light emitted (RLU). For this experiment the addition of the nucleotides was such that the SNP was represented in 3 consecutive peaks (marked). The experimental conditions are as described in Example 5.

Figure 8B:
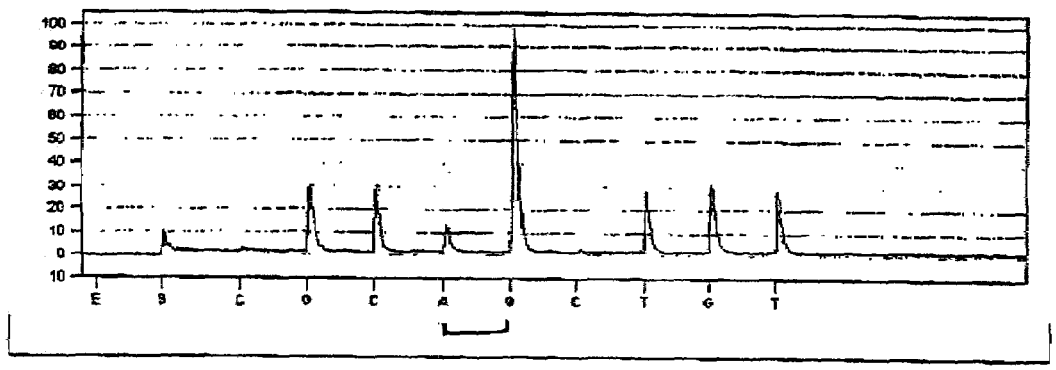

FIG. 8b shows DNA sequencing on pooled genomic DNA over SNP 345F (A/GGGG). 30 µl of PCR product was incubated with 10 µl magnetic beads and 20 µl of 2×BW buffer. Pyrosequencing™ was then performed on a PSQ™96 system instrument using Pyrosequencing™ SNP reagent kit. The resultant emitted light caused by nucleotide incorporation was measured and plotted as nucleotide incorporation V light emitted (RLU). For this experiment the addition of the nucleotides was such that the SNP was represented in only 2 consecutive peaks (marked). The experimental conditions are as described in Example 5.

Figure 9:
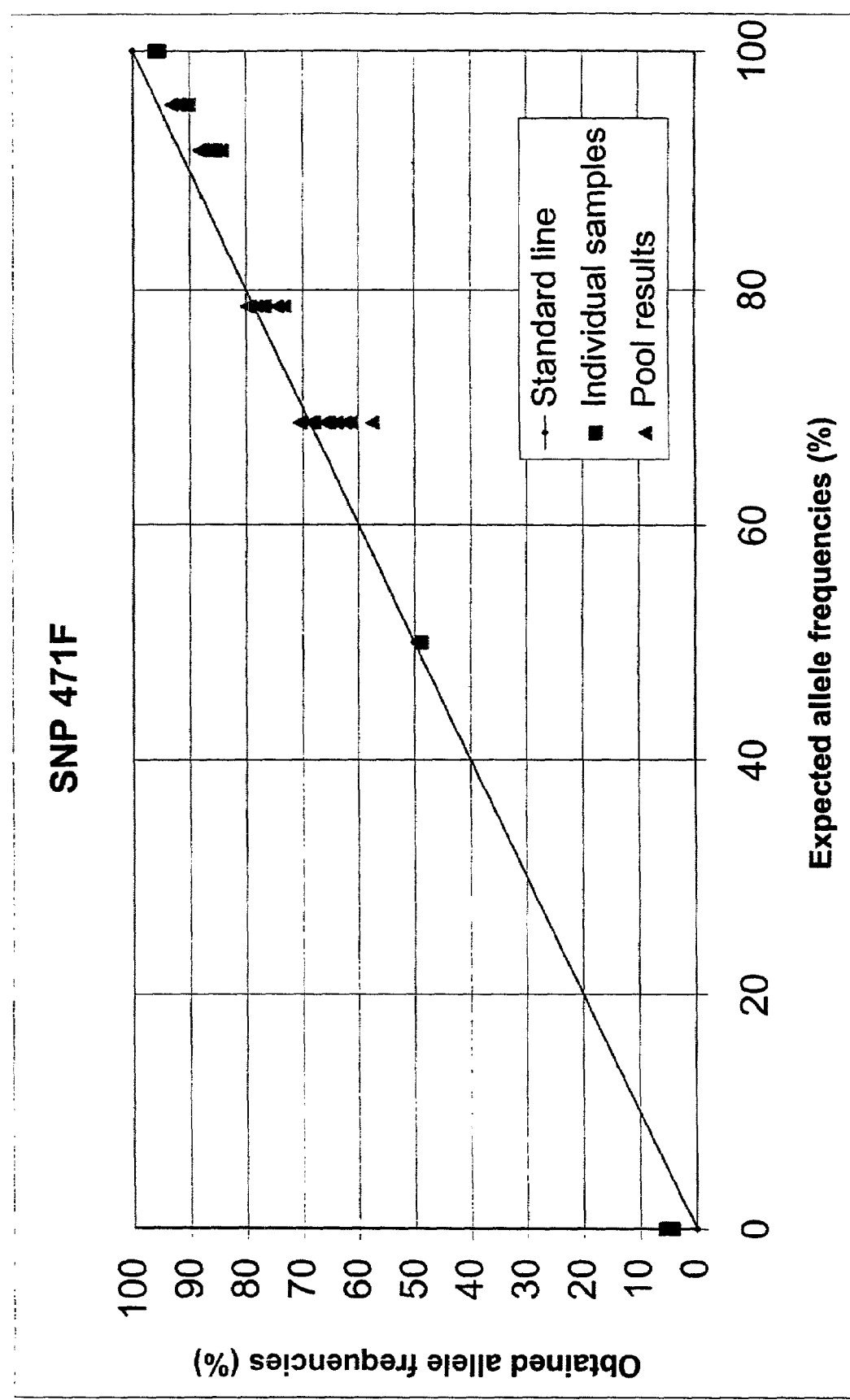

FIG. 9 depicts the obtained mean allele frequency results from Pyrosequencing™ for SNP 471F and the expected allele frequency for the sample. The results are plotted as mean allele frequency (calculated from 10 replicates) (%) versus expected allele frequencies (%). The standard line shows an imaginary pattern for an "ideal" SNP. 30 µl of PCR product was used for Pyrosequencing™, as described in Example 5. Four pools were collated, with expected allele frequencies of 68.7%, 78.6%, 91.7% and 95.5% C.

Figure 10A:
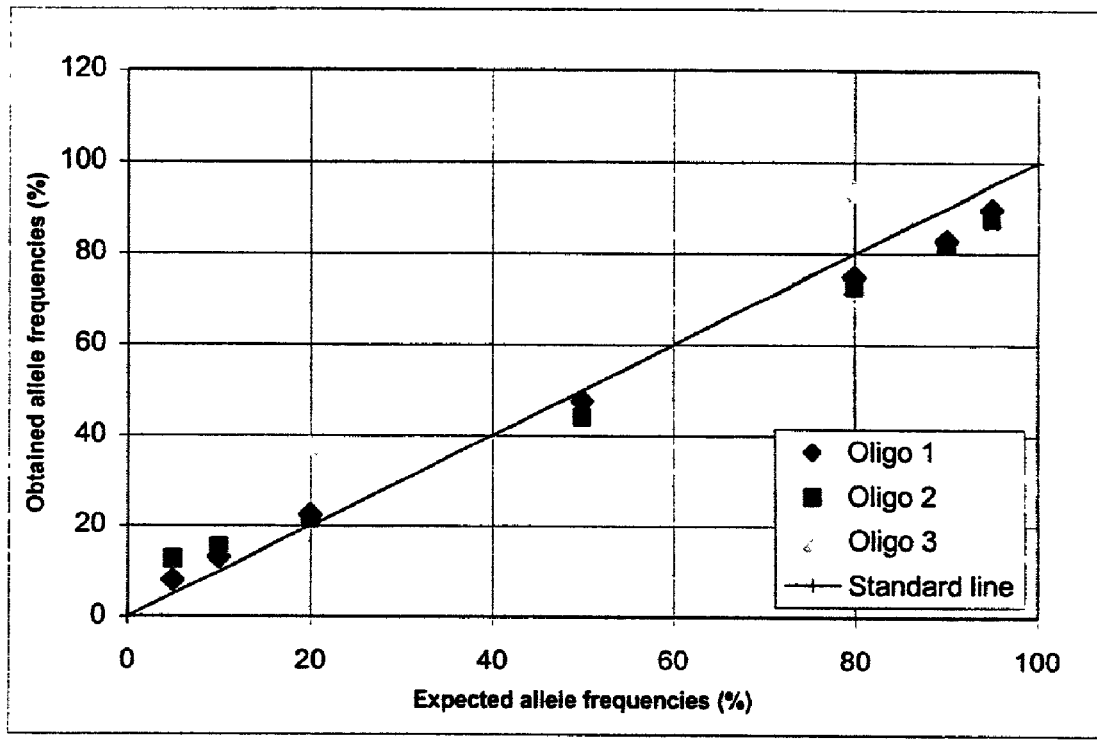

FIG. 10a depicts the allele frequency obtained via Pyrosequencing™ compared to the expected allele frequency for that pool, in percentage. 3 artificial oligonucleotides were investigated, and the results for all 3 oligonucleotides are depicted. The plot is obtained allele frequency vs expected allele frequency. The oligonucleotides were used at a concentration of 1 pmol/µl, and Pyrosequencing was performed as described in Example 5. The mean frequency was calculated from 10 replicate experiments.

Figure 10B:
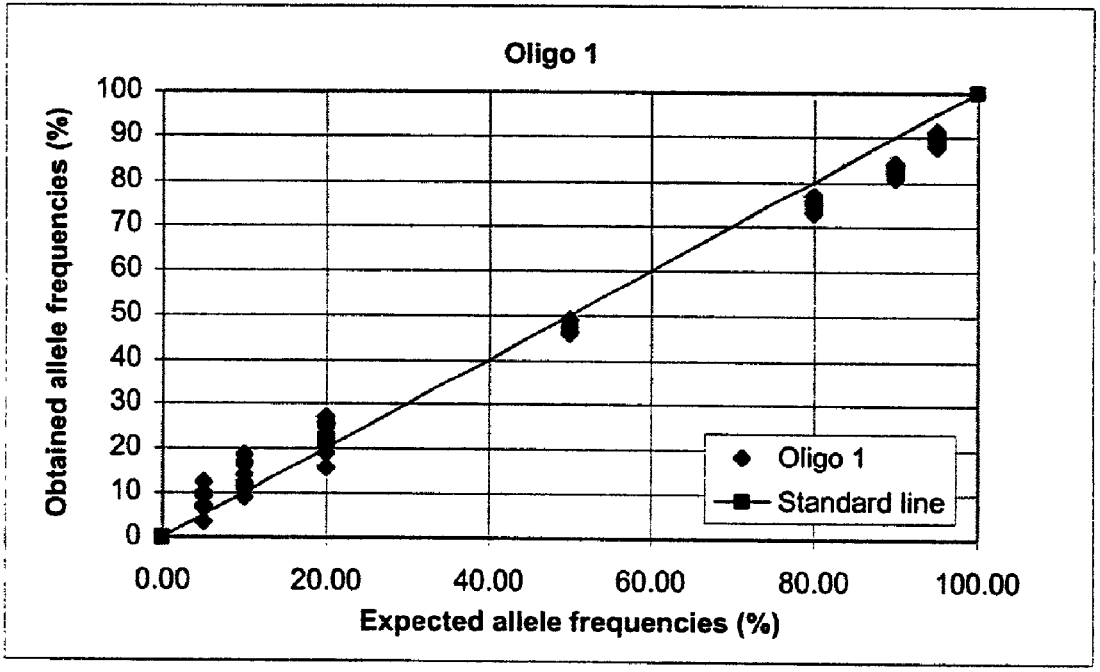

FIG. 10b depicts the results obtained for oligo 1, as shown on FIG. 10a.

Figure 10C:
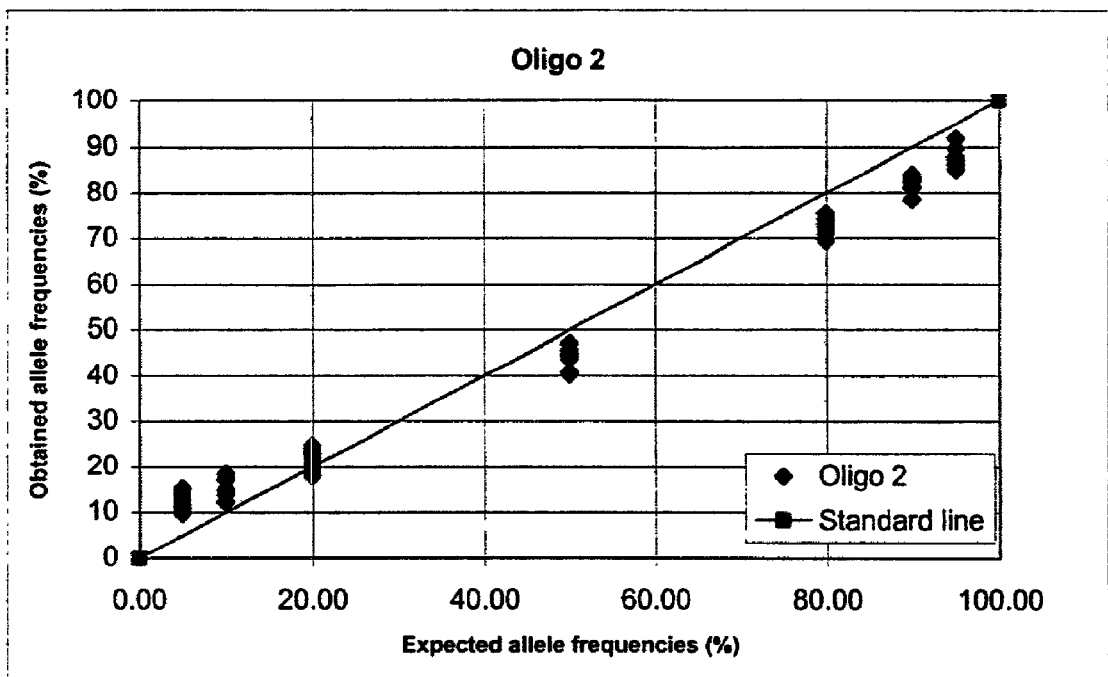

FIG. 10c depicts the results obtained for oligo 2, as shown on FIG. 10a.

Figure 10D:
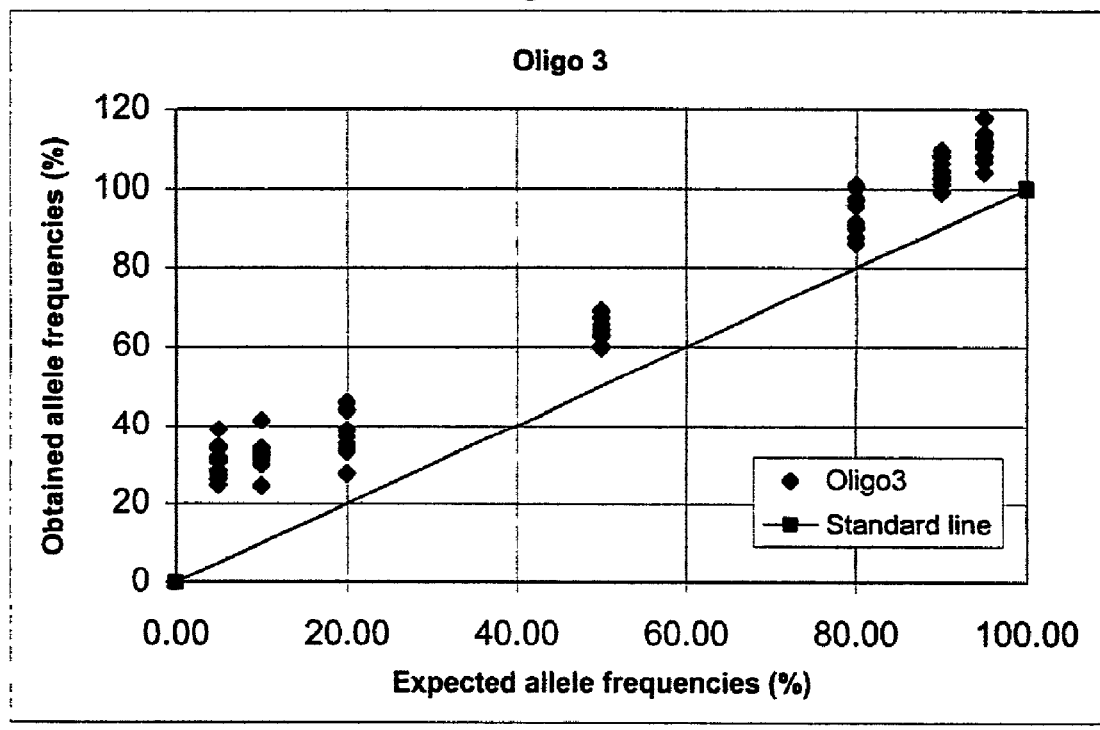

FIG. 10d depicts the results obtained for oligo 3, as shown on FIG. 10a.

Figure 11A:
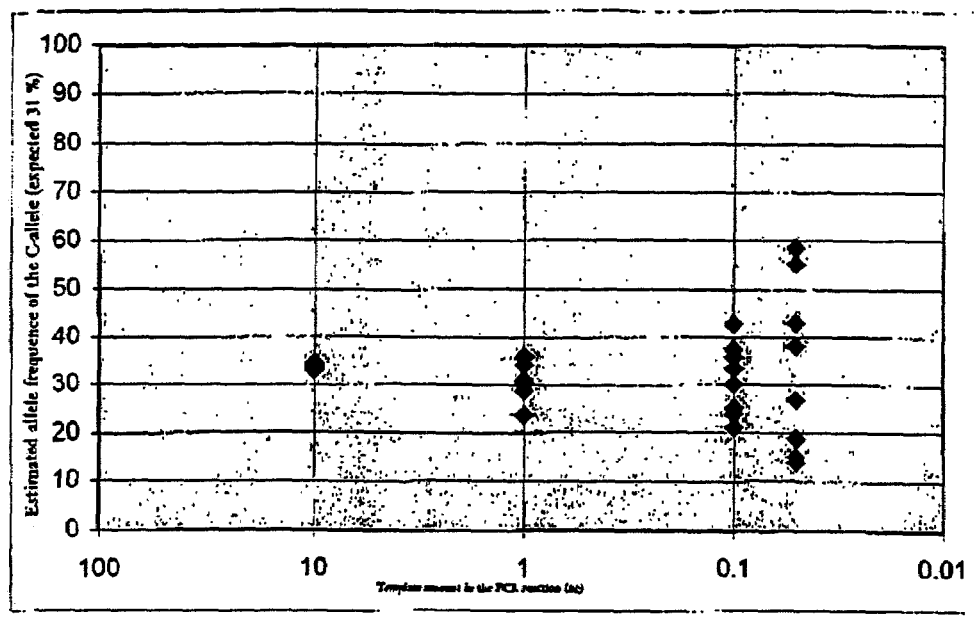

FIG. 11a represents graphically estimated allele frequency for the C allele of SNP 465R versus template amount in the PCR reaction, the allele frequency was determined via Pyrosequencing™. 4 pools with the same allele frequency were set up using long, 10 ng, 1 ng, 0.1 ng and 0.05 ng of genomic DNA prior to PCR. The experimental conditions are as described in Example 6. The expected frequency of the C allele for each of the 4 pools was 31%.

Figure 11B:
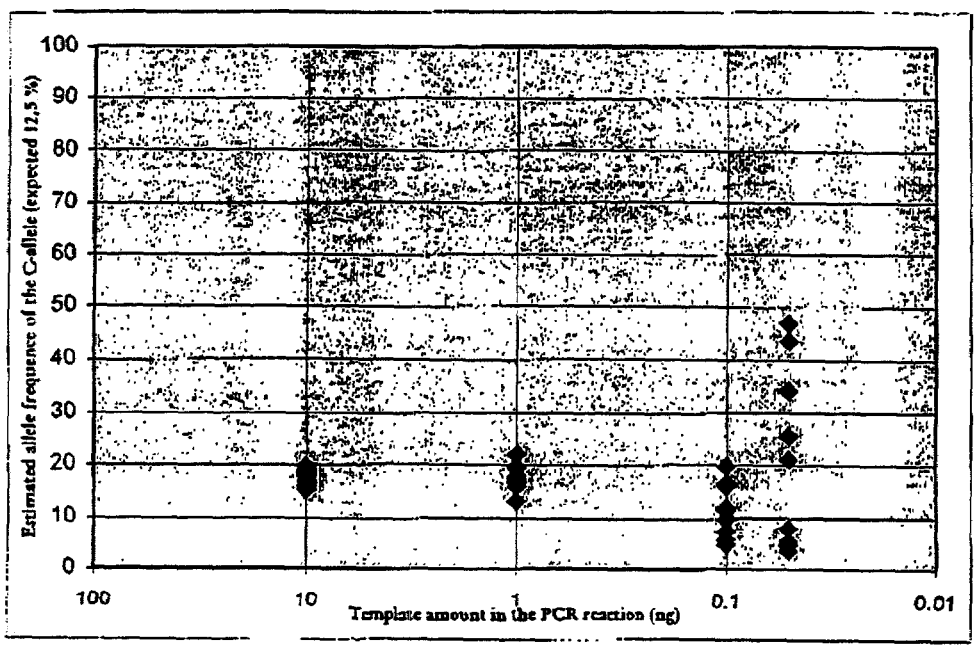

FIG. 11b represents graphically estimated allele frequency for the C allele of SNP 465R versus template amount in the PCR reaction, the allele frequency was determined via Pyrosequencing™. 4 pools with the same allele frequency were set up using long, 10 ng, 1 ng, 0.1 ng and 0.05 ng of genomic DNA prior to PCR. The experimental conditions are as described in Example 6. The expected frequency of the C allele for each of the 4 pools was 12.5%.

Figure 11C:
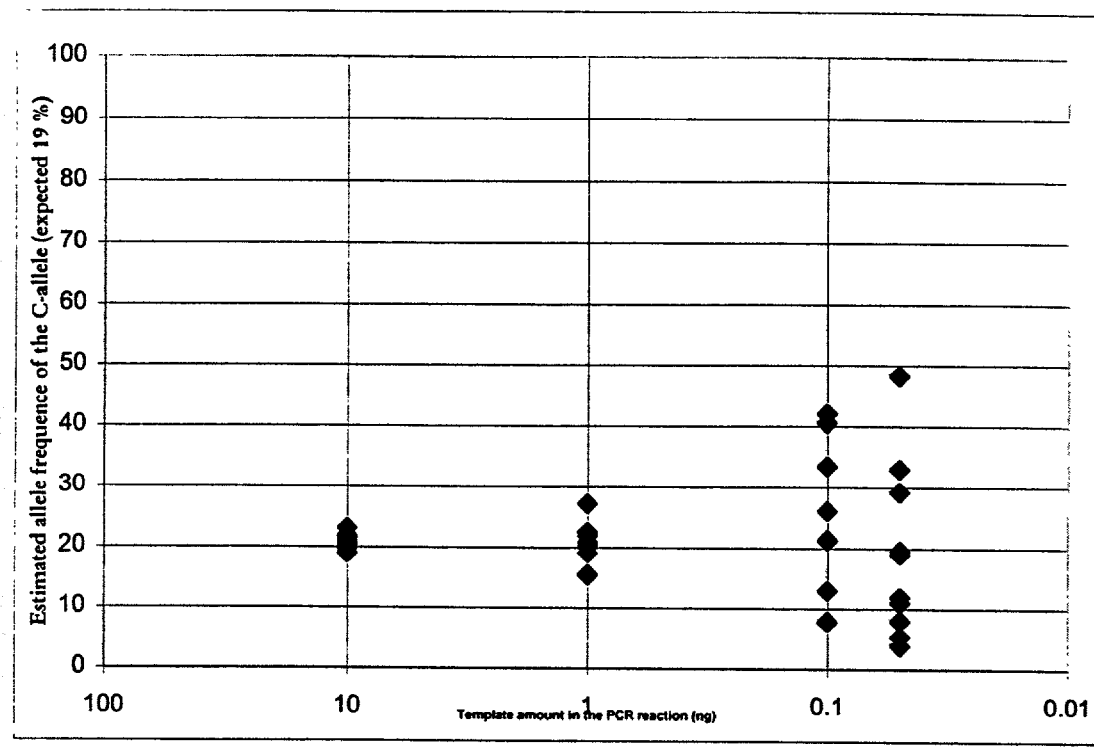

FIG. 11c represents graphically estimated allele frequency for the C allele of SNP 465R versus template amount in the PCR reaction, the allele frequency was determined via Pyrosequencing™. 4 pools with the same allele frequency were set up using 10 ng, 1 ng, 0.1 ng and 0.05 ng of genomic DNA prior to PCR. The experimental conditions are as described in Example 6. The expected frequency of the C allele for each of the 4 pools was 19%.

Figure 11D:
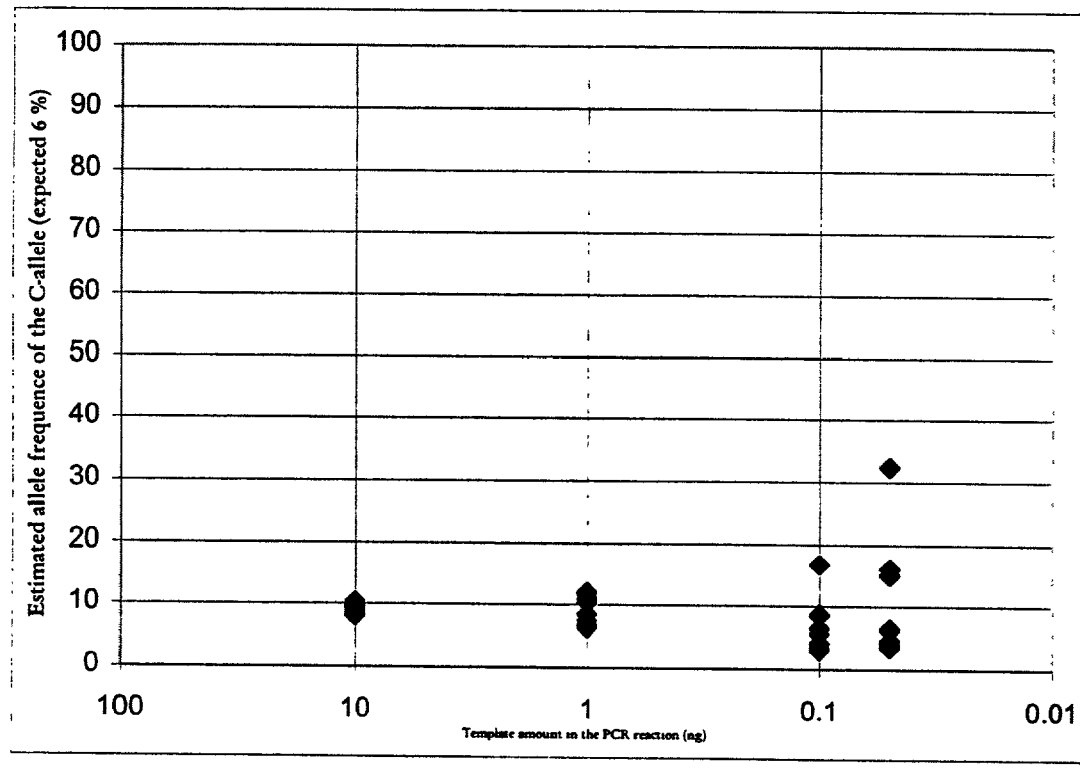

FIG. 11d represents graphically estimated allele frequency for the C allele of SNP 465R versus template amount in the PCR reaction, the allele frequency was determined via Pyrosequencing™. 4 pools with the same allele frequency were set up using long, 10 ng, 1 ng, 0.1 ng and 0.05 ng of genomic DNA prior to PCR. The experimental conditions are as described in Example 6. The expected frequency of the C allele for each of the 4 pools was 6%.

Figure 12:
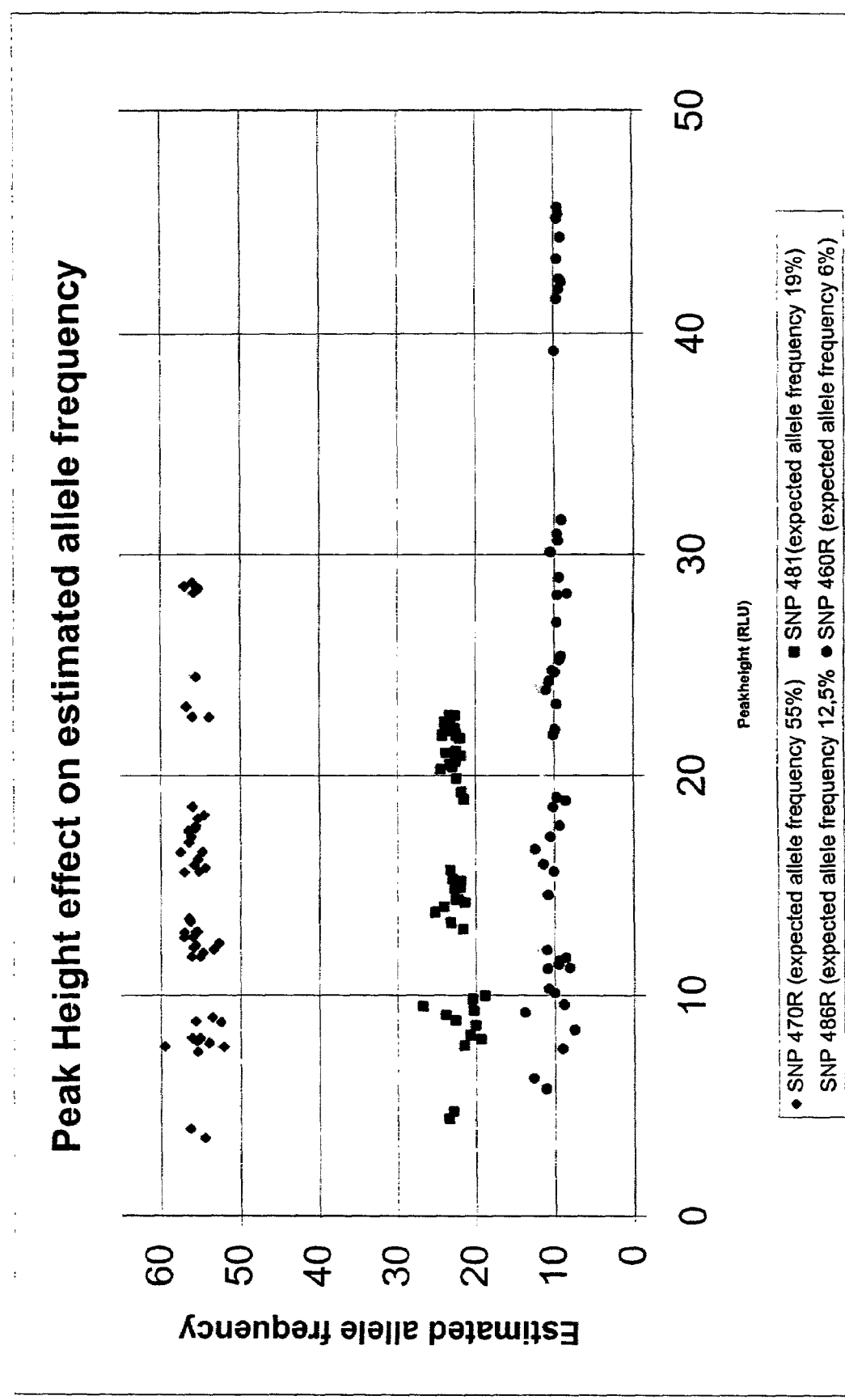

FIG. 12 represents graphically estimated allele frequency obtained via Pyrosequencing™ versus peak height obtained via Pyrosequencing™. 4 different SNPs were investigated—481R, 486R, 460R and 470R. The expected allele frequencies were as follows: 470R—55% A, 481R—19.5% G, 486R—12.5% C and 460R, 6% G. Pyrosequencing™ was performed on 5 different amounts of PCR product of pooled DNA: 30 µl, 20 µl, 15 µl, 10 µl and 5 µl. The experimental conditions are as described in Example 6.

DETAILED DESCRIPTION OF THE INVENTION

Accordingly, the present invention provides a method of determining the frequency of an allele in a population of nucleic acid molecules, said method comprising:

pooling the nucleic acid molecules of said population, performing primer extension reactions using a primer which binds at a predetermined site located in said nucleic acid molecules, and obtaining a pattern of nucleotide incorporation.

Further, the present invention provides a method of determining the amount of an allele in a sample of nucleic acid molecules, said method comprising:

performing primer extension reactions on said nucleic acid molecules, using a primer which binds at a predetermined site located in at least one said molecule, and determining which and/or how many nucleotides are incorporated in said reaction, and analysing said nucleotide incorporation information thus obtained in order to determine the amount of occurrence of said allele in said sample.

The nucleic acid molecules mentioned in the allele quantification method above may be obtained from one individual, i.e. an individual who is suspected to have additional genes, chromosomes or genomes present (i.e. trisomy or duplication of chromosomes). The nucleic acid molecules of the sample thus contain, or are suspected to contain, 3 or more alleles (e.g. 3, 4, 5 alleles). The method of the invention thus quantifies the number of alleles present (and hence the number of nucleic acid molecules which contain them), thus allowing diagnosis of gene, chromosome or whole genome duplications (or other multiplications). Thus, for example, an individual with a particular trisomy will contain 3 copies of chromosomes instead of 2. Accordingly a sample from that individual will contain 3 nucleic acid molecules corresponding to, or deriving from that chromosome, rather than two. By quantifying the amount of an allele present in that molecule, the amount of the molecule, and hence the chromosome number may be determined. In analogous fashion other duplications (i.e. replications or multiplications or indeed loss of chromosomes (e.g. chromosome number abnormalities), genes, genomes or other nucleotide sequences) may be determined. In this method an allelic variant or a particular allele may be used as a marker of a particular gene or chromosome or gene or other genetic (i.e. nucleotide) sequence it is desired to quantify.

Primer extension reactions are thus performed using the nucleic acid molecules in the pool or sample as templates. The primer, which is designed or selected to bind at a particular site in the template (e.g. adjacent, or upstream or downstream of, e.g. near to a test SNP of interest) is simply added to the sample (e.g. pooled sample for allele frequency determination) and will bind to the different template molecules present. Primer extension reactions (e.g. performed using polymerase and added nucleotides) are thus performed simultaneously or substantially simultaneously. By detecting the incorporation or non-incorporation of a given added nucleotide, a "pattern" of nucleotide incorporation may be determined which may be used to provide data which is informative on the nature of the alleles in question, and on their frequency, or occurrence (e.g. presence or absence) in the tested population. Thus, data, which may be quantitative and/or qualitative, may be obtained which may be correlated to (or which may provide information relating to) the frequency of an SNP allele (i.e. the "test" or "target" SNP or "test" or "target" allele) in the tested population. In other words, the method of the invention may be used to obtain quantitative and/or qualitative data on nucleotide incorporation relating to the SNP or allelic variant of interest.

As will be described further below, the nucleotide incorporation may be detected in various ways, and different ways of performing the primer extension reaction are possible. For example, the different nucleotides (i.e. having the different bases (e.g. A, T, C or G) may be added together, in a form in which they are distinguishable from one another (e.g. by being provided with distinguishable detectable moieties e.g. labels). More preferably however, different nucleotides may be added individually, e.g. in turn (i.e. sequentially) and the incorporation or non-incorporation of each nucleotide determined. As will be described further below, depending on the detection system selected, and/or on the target allele/SNP under test, it may not be necessary to add or use all four nucleotides (i.e. all of A, T, C or G), but a desired selection thereof.

The term "allele frequency" as used herein refers to the level or occurrence, or more particularly, the percentage of a particular allele in a given population. An allele is one of several alternative forms of a gene or nucleotide sequence at a specific chromosomal location. An allele can be any genetic variation at a given position within the nucleic acid sample. As explained above, an allele may be represented by one or more base changes at a given locus (e.g. an SNP). At each autosomal locus a diploid individual possesses 2 alleles, one maternally inherited, the other paternally. Particularly, the allele frequency determination method of the invention includes methods for determining SNP or other allelic variant allele frequencies. Each diploid individual possesses 2 alleles at a given locus. If both of the alleles are identical, the individual is homozygous for that locus. If the alleles are different, the individual is heterozygous for that locus. In the method of the invention, the frequency of each allele in the population is determined, but data on the genotype (i.e. whether the individual is homozygous for a particular allele) of a particular individual in the population will not be determined by this method.

Where allele frequency determination (i.e. allele quantification) is performed on a single sample (e.g. a sample from a single individual, for example with suspected chromosome number abnormality (e.g. trisomy) no pooling is needed.

The term "biallelic marker" as used herein refers to a genetic marker which only occurs in two forms in the population. SNPs are normally biallelic markers, although some triallelic or tetra-allelic SNPs are known and therefore the method of the invention will determine the frequency of each of the two or three or four possible alleles ("allelic variants") in a given population.

The term "population" as used herein refers to a collection of individuals, or a group. For example, the individual could be a cell, in which case the population would be a collection of cells from one or more entities or from different sites of a multi-cellular organism, or indeed cells at different stages (e.g. life stages of an organism or at different stages of the cell cycle) or a population of cells of a unicellular organism (e.g. a prokaryote). Alternatively, the individual may be a cell component, i.e. mitochondria. Further, the population may comprise individuals of the same species (i.e. humans, domestic animals, livestock animals, plants etc.) who may or may not inhabit the same areas, region or country. The population may be selected on the basis of nationality, ethnic background, disease status, or on the basis of any other classification. Further, the population may be selected on the basis of disease susceptibility (i.e. at risk of developing cardiovascular disease) or on the basis of lack of susceptibility to disease. Familial populations (i.e. all living members of one family group or sub-division of a family, e.g. particular sibling groups) may be used. A "population" may also comprise a sample of a particular cell type or tissue from different individuals e.g. a tumour, or particular organ etc. Thus, a population may comprise nucleic acid molecules derived from a particular tissue type or diseased tissue from a number of different individuals having or exhibiting that tissue or cell type, or tumour etc. The "population" as defined herein may comprise any number of individuals, from 2 or more, to several thousand (i.e. 2 to 10,000, 2 to 8,000, 2 to 5,000).

For the analysis of gene, chromosome or genome number (i.e. quantification or multiplication detection), the individual is defined as "the population". The sample from an individual may contain a variant amount or number of a given (e.g. target) nucleic acid molecule. This allele quantification can be performed on single samples which may contain a variable number or amount of a target nucleic acid molecule (target allele).

The term "pooled nucleic acid molecules" as used herein refers to the pooling of nucleic acid molecules into one reaction mixture from all individuals of a given population (i.e. the adding together of the different or individual nucleic acid samples to create a pooled sample). Therefore, multiple individual nucleic acid molecules are pooled prior to genetic analysis. Pooling of nucleic acid molecules is sample size independent, i.e. independent of the number of samples comprising the pool.

"Multiple" as used herein means two or more e.g. 3, 4, 5, 6, 8, 10 or more, or 100, 200, 500, 1000, 2000, 5000 or 10000 or more.

Conveniently, the nucleic acid molecule may be DNA, although determining the allele frequency of RNA (e.g. mRNA) is also within the invention. If it is desired to use a RNA sample, the method may additionally include the step of generating cDNA from the RNA template, conveniently by using reverse transcriptase. Alternatively, if desired, the primer extension reactions may be performed directly on RNA templates.

The target nucleic acid may thus be any nucleic acid, isolated or synthetic, in any desired or convenient form. It may thus be genomic DNA, or isolated mRNA which may be used directly for analysis by the method of the invention, or it may be a nucleic acid product derived therefrom (or corresponding thereto), e.g. by synthesis, such as cDNA as mentioned above, or an amplification product (e.g. PCR amplicon), clones or library products etc.

In carrying out the method of the invention, a primer specific for the allele of interest is provided which binds to the nucleic acid molecules at a predetermined site. The primer is designed or selected so that when the primer extension reaction is performed, the primer is extended over the allele (or SNP) in the nucleic acid. In other words, the primer binds to the nucleic acid molecule at, or near to (e.g. within 1 to 20, 1 to 10 or 1 to 6 bases), the allele/SNP.

It will be understood that in order to perform the invention the primer binding site should be available in all individual nucleic acid molecules in the pooled population. Such primer binding sites will therefore advantageously lie in regions which are common to, or substantially conserved between the different individuals in the population. This may readily be achieved by selecting the primer binding site to lie in conserved/semi-conserved regions as discussed above.

It will therefore be understood that in the pooled nucleic acid, there will generally be 2 "allelic variants" present for each SNP. Thus, at a given polymorphic position, the nucleotide may be either one or two possible bases. In the case of triallelic SNP, there will be one of 3 possible bases. In the case of tetra-allelic SNPs there will be one or two of four possible bases.

Preferably, the polymorphic position is not sequenced within a homopolymeric stretch in either allelic variant. As used herein a homopolymeric stretch is defined as a stretch of nucleic acid which contains two or more (i.e. 3 or more, 4 or more or 5 or more) consecutive identical nucleotides (i.e. $GC_{AAA}T$). However, primers can be designed to avoid sequencing the homopolymeric stretch whilst obtaining data on the allele frequency. Therefore, with well designed primers, estimating allele frequencies of alleles present in homopolymeric stretches is within the scope of the invention. It is possible to design the primer in order to avoid sequencing the repeated bases. The extension primer can thus be designed to cover the homopolymeric region.

Further, by the use of appropriate controls or conditions, and depending on the detection method chosen, it is possible to determine the frequency of an allele if the SNP is in a homopolymeric stretch.

The primer extension reactions conveniently may be performed by sequentially adding nucleotides to the reaction mixture (i.e. polymerase and primer/template mixture). Advantageously, the different nucleotides are added in known predetermined order. As each nucleotide is added, it may be determined whether or not nucleotide incorporation takes place.

Advantageously, as described in more detail below, the amount of nucleotide incorporated (i.e. how many nucleotide residues) may be determined. Such a quantitative embodiment, wherein nucleotide incorporation is determined quantitatively, represents a preferred aspect of the invention.

In this manner, sequencing data may be obtained for the polymorphic position in all nucleic acid molecules in the pooled samples. This sequencing data comprises the base identity (i.e. sequence) of the particular SNP residue, together with quantitative data on how many nucleotides of each type have been incorporated. In other words, the data corresponds to the allele frequency for the given SNP. The allele frequency may thus readily be calculated using the quantitative values obtained for nucleotide incorporation during primer extension wherein the primer is extended over the polymorphic position.

Thus, by identifying how much of each nucleotide is incorporated at the polymorphic site in a primer extension reaction, it is possible to calculate the frequency of each allele.

In order to perform the invention, it may be advantageous or convenient first to amplify the nucleic acid molecule by any suitable amplification method known in the art. The target nucleic acid would then be an amplicon. Suitable in vitro amplification techniques include any process which amplifies the nucleic acid present in the reaction under the direction of appropriate primers. The amplicon method may thus preferably be PCR, or any of the various modifications thereof e.g. the use of nested primers, although it is not limited to this method. Those skilled in the art will appreciate that other amplification procedures may also be used, such as Self-sustained Sequence Replication (3SR), NASBA, the Q-beta replicase amplification system and Ligase chain reaction (LCR) (see for example Abramson and Myers (1993) Current Opinion in Biotech., 4: 41–47). If PCR is used to amplify the nucleic acid, suitable primers, are designed to ensure that the region of interest within the nucleic acid sequence (i.e. the region containing the SNP), is amplified. PCR can also be used for indiscriminate amplification of all nucleic acid sequences, allowing amplification of essentially all sequences within the sample for study (i.e. total nucleic acid). Linker-primer PCR is particularly suitable for indiscriminate amplification, and uses double stranded oligonucleotide linkers with a suitable overhanging end, which are ligated to the ends of target nucleic acid fragments. Amplification is then conducted using oligonucleotide primers which are specific for the linker sequences. Alternatively, completely random oligonucleotide primers may be used in conjunction with DOP-PCR (degenerate oligonucleotide-primed) to amplify all the nucleic acid within a sample.

One or more of the amplification primers used in the amplification reaction, may be subsequently used as an "extension primer", but this will preferably be a different primer. It will be appreciated that the sequence and length of the oligonucleotide amplification and extension primers to be used in the amplification and extension steps, respectively, will depend on the sequence of the target nucleic acid, the desired length of amplification or extension product, the further functions of the primer (i.e. for immobilization) and the method used for amplification and/or extension. Appropriate primers may readily be designed applying principles and techniques well known in the art.

Advantageously, as mentioned above, an extension primer will bind substantially adjacent (e.g. within 1–20, 1–10 or 1–6, preferably within 1–3 bases), or exactly adjacent to the SNP of the target nucleic acid molecules and may be complementary to a conserved or semi-conserved region of the nucleic acid molecules. In order for the method of the invention to be performed, knowledge of the sequence surrounding the allele (e.g. of the conserved or semi-conserved region) is required in order to design an appropriate complementary extension primer. The specificity is achieved by virtue of complementary base pairing. For all embodiments of the invention, primer design may be based upon principles well known in the art. It is not necessary for the extension or amplification primer to have absolute complementarity to the binding site, but this is preferred to improve the specificity of binding.

The extension primer may be designed to bind to the sense or anti-sense strand of the target nucleic acid.

The "primer extension" reaction according to the invention includes all forms of template-directed polymerase-catalysed nucleic acid synthesis reactions. Conditions and reagents for primer extension reactions are well known in the art, and any of the standard methods, reagents and enzymes etc. may be used in this step (see e.g. Sambrook et al., (eds), Molecular Cloning: a laboratory manual (1989), Cold Spring Harbor Laboratory Press). Thus, the primer extension reaction at its most basic, is carried out in the presence of primer, deoxynucleotides (dNTPs) and a suitable polymerase enzyme e.g. T7 polymerase, Klenow or Sequenase Ver 2.0 (USB USA), or indeed any suitable available polymerase enzyme. As mentioned above, for an RNA template, reverse transcriptase may be used. Conditions may be selected according to choice, having regard to procedures well known in the art.

The primer is thus subjected to a primer-extension reaction in the presence of a nucleotide, whereby the nucleotide is only incorporated if it is complementary to the base immediately adjacent (3') to the primer position. The nucleotide may be any nucleotide capable of incorporation by a polymerase enzyme into a nucleic acid chain or molecule. Thus, for example, the nucleotide may be a deoxynucleotide (dNTP, deoxynucleoside triphosphate) or dideoxynucleotide (ddNTP, dideoxynucleoside triphosphate). Thus, the following nucleotides may be used in the primer-extension reaction: guanine (G), cytosine (C), thymine (T) or adenine (A) deoxy- or dideoxy-nucleotides. Therefore, the nucleotide may be dGTP (deoxyguanosine triphosphate), dCTP (deoxycytidine triphosphate), dTTP (deoxythymidine triphosphate) or dATP (deoxyadenosine triphosphate). As discussed further below, suitable analogues of DATP, and also for dCTP, dGTP and dTTP may also be used. Thus, modified nucleotides, or nucleotide derivatives (e.g. chemically modified nucleotides) may be used so long as they are capable of incorporation by a polymerase enzyme. Dideoxynucleotides may also be used in the primer-extension reaction. The term "dideoxynucleotide" as used herein includes all 2'-deoxynucleotides in which the 3' hydroxyl group is modified or absent. Dideoxynucleotides are capable of incorporation into the primer in the presence of the polymerase, but cannot enter into a subsequent polymerisation reaction, and thus function as a "chain terminator". It will therefore be appreciated that in embodiments of the invention which rely on sequential nucleotide addition the use of chain terminating nucleotides is to be avoided (although so-called "false" or "labile" terminators might be used in which the 3' blocking group may be removed following incorporation. Such modified nucleotides are known and described in the art). However, in some embodiments of the invention it may be advantageous to use chain terminating nucleotides whereby it is desired to terminate sequencing of one allele after incorporation of the chain terminating nucleotide, but more sequence information is required for the other allele.

If the nucleotide is complementary to the target base, the primer is extended by one nucleotide, and inorganic pyrophosphate is released. As discussed further below, in a preferred method, the inorganic pyrophosphate may be detected in order to detect the incorporation of the added nucleotide. For the SNP of interest, the addition of two nucleotides will be sufficient to generate allele frequency information. The primer bound to one allelic variant will be extended by 1 nucleotide upon addition of the nucleotide which base pairs to the nucleotide in the polymorphic position. The primer bound to the other allelic variant will therefore not be extended by addition of this nucleotide. This primer will be extended in the next round of nucleotide addition, which should be designed to be a complementary base to the allelic variant (i.e. if the allelic variant is C, a G should be added). Different nucleotides may be added sequentially, advantageously in known order, as discussed above, to reveal the nucleotides which are incorporated for each extension primer. Accordingly, determining the number of nucleotides incorporated for each nucleotide addition, will reveal the frequency of that allele corresponding to nucleotide incorporation and hence contribute to the calculation of allele frequency.

Hence, a primer extension protocol may involve annealing a primer as described above, adding a nucleotide, performing a polymerase-catalysed primer extension reaction, detecting the presence or absence of incorporation of said nucleotide (and advantageously also determining the amount of each nucleotide incorporated) and repeating the nucleotide addition and primer extension steps etc. one or more times. As discussed above, single (i.e. individual) nucleotides may be added successively to the same primer-template mixture.

In order to permit the repeated or successive (iterative) addition of nucleotides in a primer-extension procedure, the previously-added nucleotide must be removed. This may be achieved by washing, or more conveniently, by using a nucleotide-degrading enzyme, for example as described in detail in WO98/28440.

Accordingly, in a principal embodiment of the present invention, a nucleotide degrading enzyme is used to degrade any unincorporated or excess nucleotide. Thus, if a nucleotide is added which is not incorporated (because it is not complementary to the target base), or any added nucleotide remains after an incorporation event (i.e. excess nucleotides) then such unincorporated nucleotides may readily be removed by using a nucleotide-degrading enzyme. This is described in detail in WO98/28440.

The term "nucleotide degrading enzyme" as used herein includes any enzyme capable of specifically or non-specifically degrading nucleotides, including at least nucleoside triphosphates (NTPs), but optionally also di- and mono-phosphates, and any mixture or combination of such enzymes, provided that a nucleoside triphosphatase or other NTP-degrading activity is present. Where a chain terminating nucleotide is used (e.g. a dideoxy nucleotide is used), the nucleotide degrading enzyme should also degrade such a nucleotide. Although nucleotide-degrading enzymes having a phosphatase activity may conveniently be used according to the invention, any enzyme having any nucleotide or nucleoside degrading activity may be used, e.g. enzymes which cleave nucleotides at positions other than at the phosphate group, for example at the base or sugar residues. Thus, a nucleoside triphosphate degrading enzyme is essential for the invention. Nucleoside di- and/or mono-phosphate degrading enzymes are optional and may be used in combination with a nucleoside tri-phosphate degrading enzyme.

The preferred nucleotide degrading enzyme is apyrase, which is both a nucleoside diphosphatase and triphosphatase, catalysing the reactions NTP→NDP+Pi and NDP→NMP+Pi (where NTP is a nucleoside triphosphate, NDP is a nucleoside diphosphate, NMP is a nucleotide monophosphate and Pi is inorganic phosphate). Apyrase may be obtained from the Sigma Chemical Company. Other possible nucleotide degrading enzymes include Pig Pancreas nucleoside triphosphate diphosphorydrolase (Le Bel et al., 1980, J. Biol. Chem., 255, 1227–1233). Further enzymes are described in the literature.

The nucleotide-degrading enzyme may conveniently be included during the polymerase (i.e. primer extension) reaction step. Thus, for example the polymerase reaction may conveniently be performed in the presence of a nucleotide-degrading enzyme. Although less preferred, such an enzyme may also be added after nucleotide incorporation (or non-incorporation) has taken place, i.e. after the polymerase reaction step.

Thus, the nucleotide-degrading enzyme (e.g. apyrase) may be added to the polymerase reaction mixture (i.e. target nucleic acid, primer and polymerase) in any convenient way, for example prior to or simultaneously with initiation of the reaction, or after the polymerase reaction has taken place, e.g. prior to adding nucleotides to the sample/primer/polymerase to initiate the reaction, or after the polymerase and nucleotide are added to the sample/primer mixture.

Conveniently, the nucleotide-degrading enzyme may simply be included in the reaction mixture for the polymerase reaction, which may be initiated by the addition of the nucleotide.

According to the present invention, detection of nucleotide incorporation can be performed in a number of ways, such as by incorporation of labelled nucleotides which may subsequently be detected, or by using labelled probes which are able to bind to the extended sequence.

The method may be performed using a Sanger sequencing method combined with a standard detection strategy, e.g. electrophoresis or mass spectrometry to analyse, or determine, nucleotide incorporation. However, it is preferred to use a sequencing-by-synthesis method, due to the fact that the extension reactions are quantitative, i.e. that the nucleotide incorporation may be determined quantitatively. As mentioned above, sequencing-by-synthesis methods are disclosed extensively in U.S. Pat. No. 4,863,849, which discloses a number of ways in which nucleotide incorporation may be determined or detected, e.g. spectrophotometrically or by fluorescent detection techniques, for example by determining the amount of nucleotide remaining in the added nucleotide feedstock, following the nucleotide incorporation step. Alternatively, labelled nucleotides may be utilised in the nucleotide incorporation step. Such labelled nucleotides may be chain terminating or capable of further extension. The nucleotide incorporated may be identified and the label removed or neutralised prior to the incorporation of the next labelled nucleotide. Such a method is described in U.S. Pat. No. 6,087,095 of Rosenthal et al. This patent also describes sequencing-by-synthesis on a solid phase (e.g. beads). The label may be a fluorescent label or a radioactive label.

The preferred method of sequencing-by-synthesis is however a pyrophosphate detection-based method.

Preferably, therefore, nucleotide incorporation is detected by detecting PPi release, preferably by luminometric detection, and especially by bioluminometric detection.

PPi can be determined by many different methods and a number of enzymatic methods have been described in the literature (Reeves et al., (1969), Anal. Biochem., 28, 282–287; Guillory et al., (1971), Anal. Biochem., 39, 170–180; Johnson et al., (1968), Anal. Biochem., 15, 273; Cook et al., (1978), Anal. Biochem. 91, 557–565; and Drake et al., (1979), Anal. Biochem. 94, 117–120).

It is preferred to use luciferase and luciferin in combination to identify the release of pyrophosphate since the amount of light generated is substantially proportional to the amount of pyrophosphate released which, in turn, is directly proportional to the amount of nucleotide incorporated. The amount of light can readily be estimated by a suitable light sensitive device such as a luminometer. Thus, luminometric methods offer the advantage of being able to be quantitative.

Luciferin-luciferase reactions to detect the release of PPi are well known in the art. In particular, a method for continuous monitoring of PPi release based on the enzymes ATP sulphurylase and luciferase has been developed (Nyrén and Lundin, Anal. Biochem., 151, 504–509, 1985; Nyrén P., Enzymatic method for continuous monitoring of DNA polymerase activity (1987) Anal. Biochem Vol 167 (235–238)) and termed ELIDA (Enzymatic Luminometric Inorganic Pyrophosphate Detection Assay). The use of the ELIDA method to detect PPi is preferred according to the present invention. The method may however be modified, for example by the use of a more thermostable luciferase (Kaliyama et al., 1994, Biosci. Biotech. Biochem., 58, 1170–1171) and/or ATP sulfurylase (Onda et al., 1996, Bioscience, Biotechnology and Biochemistry, 60:10, 1740–42). This method is based on the following reactions:

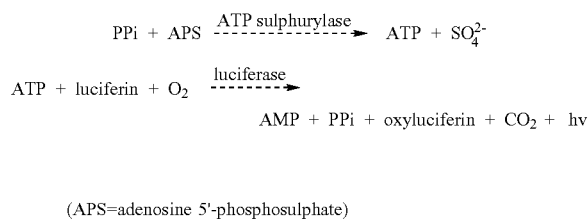

(APS=adenosine 5'-phosphosulphate)

Reference may also be made to WO 98/13523 and WO 98/28448, which are directed to pyrophosphate detection-based sequencing procedures, and disclose PPi detection methods which may be of use in the present invention.

In a PPi detection reaction based on the enzymes ATP sulphurylase and luciferase, the signal (corresponding to PPi released) is seen as light. The generation of the light can be observed as a curve known as a Pyrogram™. Light is generated by luciferase action on the product, ATP (produced by a reaction between PPi and APS (see below) mediated by ATP sulphurylase) and, where a nucleotide-degrading enzyme such as apyrase is used, this light generation is then "turned off" by the action of the nucleotide-degrading enzyme, degrading the ATP which is the substrate for luciferase. The slope of the ascending curve may be seen as indicative of the activities of DNA polymerase (PPi release) and ATP sulphurylase (generating ATP from the PPi, thereby providing a substrate for luciferase). The height of the signal is dependent on the activity of luciferase, and the slope of the descending curve is, as explained above, indicative of the activity of the nucleotide-degrading enzyme. As explained below, in a Pyrogram™ in the context of a homopolymeric region, peak height is also indicative of the number of nucleotides incorporated for a given nucleotide addition step. Then, when a nucleotide is added, the amount of PPi released will depend upon how many nucleotides (i.e. the amount) are incorporated, and this will be reflected in the peak height.

The use of pyrophosphate detection-based sequencing methods, and in particular those based on the ELIDA detection enzymes, is particularly advantageous in the present invention; the correlation between signals obtained in such methods (i.e. peak heights) and SNP allele frequencies has been shown to be excellent, and the accuracy of the results obtained surprisingly high. Frequencies as lows as 5% for one allele have been determined with reasonable accuracy in pools of samples.

Advantageously, by including the PPi detection enzyme(s) (i.e. the enzyme or enzymes necessary to achieve PPi detection according to the enzymatic detection system selected, which in the case of ELIDA, will be ATP sulphurylase and luciferase) in the polymerase reaction step, the method of the invention may readily be adapted to permit extension reactions to be continuously monitored in real-time, with a signal being generated and detected, as each nucleotide is incorporated.

Thus, the PPi detection enzymes (along with any enzyme substrates or other reagents necessary for the PPi detection reaction) may simply be included in the polymerase reaction mixture.

A potential problem which has previously been observed with PPi-based sequencing methods is that dATP, used in the chain extension reaction, interferes in the subsequent luciferase-based detection reaction by acting as a substrate for the luciferase enzyme. This may be reduced or avoided by using, in place of deoxyadenosine triphosphate (ATP), a DATP analogue which is capable of acting as a substrate for a polymerase but incapable of acting as a substrate for a PPi-detection enzyme. Such a modification is described in detail in WO98/13523.

The term "incapable of acting" includes also analogues which are poor substrates for the detection enzymes, or which are substantially incapable of acting as substrates, such that there is substantially no, negligible, or no significant interference in the PPi detection reaction.

Thus, a further preferred feature of the invention is the use of a dATP analogue which does not interfere in the enzymatic PPi detection reaction but which nonetheless may be normally incorporated into a growing DNA chain by a polymerase. By "normally incorporated" is meant that the nucleotide is incorporated with normal, proper base pairing. In the preferred embodiment of the invention where luciferase is a PPi detection enzyme, the preferred analogue for use according to the invention is the [1-thio] triphosphate (or α-thiotriphosphate) analogue of deoxy ATP, preferably deoxyadenosine [1-thio] triphosphate, or deoxyadenosine-thiotriphosphate (dATP αS) as it is also known. dATP αS, along with the α-thio analogues of dCTP, dGTP and dTTP, may be purchased from Amersham Pharmacia. Experiments have shown that substituting dATP with dATP αS allows efficient incorporation by the polymerase with a low background signal due to the absence of an interaction between dATP αS and luciferase. False signals are decreased by using a nucleotide analogue in place of dATP, because the background caused by the ability of dATP to function as a substrate for luciferase is eliminated. In particular, an efficient incorporation with the polymerase may be achieved while the background signal due to the generation of light by the luciferin-luciferase system resulting from DATP interference is substantially decreased. It has been noted by the inventors that the use of dATP αS can lead to higher peaks than the use of dATP. The peak height is consistently higher, and thus if dATP αS is used, the actual 'peak height' can be calculated via a 'peak height reduction'. The dNTP αS analogues of the other nucleotides may also be used in place of the other dNTPs.

The step of detecting nucleotide incorporation by detecting PPi release results in a signal indicative of the amount of pyrophosphate released, and hence the amount of nucleotide incorporated.

In the method of the invention, the primer-extension reaction is performed simultaneously for each nucleic acid molecule in the reaction mixture. Thus, for every nucleotide addition to the reaction mixture, multiple nucleotides may be incorporated into the extended primers. The signal generated in the pyrophosphate detection step will therefore be indicative of the number of nucleotides incorporated in the primer-extension step for the combination of all primers bound to the template nucleic acid. The size of the signal (i.e. the height of each peak) can therefore be correlated directly to the number of incorporated nucleotides. Typically, the primer needs only to be subjected to 1 to 20, preferably 1 to 10, e.g. 1 to 5 and most preferably 2 to 4 cycles of nucleotide addition.

It will be understood that the order of nucleotide addition in the reaction mixture can be tailored to each SNP to ensure that the relevant allele frequency is obtained efficiently and accurately. For example, if the 2 possible allelic nucleotides are C or T (or vice versa), the order of nucleotide addition when extending the primer over the polymorphic site may be C followed by T, using the methods as described previously.

Therefore, the peaks showing nucleotide incorporation for the allelic variant bases should preferably be adjacent to each other, facilitating calculation of the allele frequencies.

As mentioned previously, the allele variants are preferably not sequenced in a homopolymeric stretch of 3 or more identical bases. It will be clear that the peak height in such a situation will represent not only the nucleotide incorporation relating to the polymorphic position, but will also represent the incorporation of 2 or more nucleotides further downstream of the polymorphism. Thus, the number of nucleotides incorporated will also reflect the number of nucleotides present in the homopolymeric region, which will be the same for each allelic variant. Therefore, it is advisable to avoid performing allele frequency determinations on SNPs wherein one allelic variant lies within a homopolymeric stretch of three or more identical bases, unless a primer can be designed as described previously.

It will be understood that in order to obtain accurate and reliable data relating to the frequency of an allele in a population, it will be preferable to use the same amount of nucleic acid for each individual in the population in the reaction mixture. Therefore, it may be necessary to calibrate the samples prior to pooling. Thus, it forms a preferred aspect of the invention to measure or determine the concentration of the nucleic acid in the sample prior to pooling. Any standard technique may be used to effect the measurement/determination of nucleic acid concentration, such as gel electrophoresis and spectrophotometry. However, these methods are not without their drawbacks, as they rely upon having a significant sample of nucleic acid to use for concentration determination. A further aspect of this invention is thus using a primer-extension reaction to calibrate the nucleic acid concentrations prior to pooling.

In order to perform primer extension reactions to calculate the concentration of nucleic acid in a sample, it will first be necessary to select a suitable SNP. A suitable SNP for such analysis will not be present in a homopolymeric sequence and will not be preferentially amplified in any PCR-type reactions. Further, the SNP should be chosen such that it gives no background signals in a primer-extension reaction, and that the signals, e.g. peak height, (see before) are even. Preferably, each of the individuals has a known sequence (genotype) at this SNP. If not, the sequence (genotype) can be determined using standard sequence-by-synthesis reaction means. One reference sample (Ref 1) is selected as the main reference from one of the homozygotes, another reference sample (Ref 2) is selected from the other homozygote, and are pooled, and the method of the invention as previously described may be carried out. The results of the primer extension reactions enable the relative concentrations of each reference sample to be calculated, as the signals (e.g. peak heights) (see before) are directly related to the amount of nucleotide incorporation. To measure the concentration of the rest of the samples in the population, these are pooled individually with one of the reference samples. Heterozygote samples should be paired with one of the homozygote references, and then analysed as mentioned previously. Thus, as the concentration of the reference sample is known, the concentration of the sample pooled with the reference sample can be easily calculated. Homozygote samples should be pooled with the other homozygote reference sample (i.e. pair AA with CC, not AA with AA).

The peak height for allele 1 (i.e. A) and the peak height for allele 2 (i.e. C) are recorded, and the following calculations are performed (for an allele not present in a homopolymer stretch):

$$Y = \frac{\text{Peak Height (allele 1)}}{\text{Peak Height (allele 1)} + \text{Peak height (allele 2)}}$$

where Y is the frequency of allele 1. The concentration in the sample is calculated by multiplying the concentration of the reference by a concentration factor (X). Therefore, X must be calculated. X is in relation to the reference sample used. If the sample is heterozygous, X is calculated in the following way:

$$X = \frac{2Y}{1 - 2Y}$$

However, if the sample is homozygous, the following calculation is used:

$$X = \frac{Y}{1 - Y}$$

Thus, once it has been decided what volume of one of the reference samples is to be used in the pool, the volume of samples to be added to the pool is calculated by dividing the volume for the reference with the X value for each sample i.e.

$$\text{volume (sample } n) = \frac{\text{volume (ref 1)}}{X \text{ (sample } n)}$$

Alternatively or additionally, once it has been decided what volume of one of the reference samples is to be used in the pool, the volume of the second reference sample is set by dividing the volume of reference 1 with the concentration factor (X) of reference 2.

$$\text{Volume (reference 2)} = \frac{\text{Volume (reference 1)}}{X \text{ (reference 2)}}$$

From these 2 volumes (reference 1 and reference 2) the volumes of samples to be added to the pool is calculated by dividing the volume for the reference with the X value for each sample. It is important to use the correct reference for each sample (i.e. the reference this sample has been compared to).

$$\text{Volume (sample } n) = \frac{\text{Volume (ref 1 or 2)}}{X \text{ (sample } n)}$$

Thus, although different volumes are used for each sample, the amount of nucleic acid from each individual will be the same. Calculations have been performed in Example 1.

The uniformity of nucleic acid amount of different individuals in the population (i.e. in the individual nucleic acid samples which are pooled) may vary, depending on the source and nature of the nucleic acid, and indeed the importance of such uniformity (and hence the need for calibration) may also vary, depending on the nucleic acid samples used. Thus, when using pooled genomic DNA samples, uniformity of DNA concentration between individual samples has been found to be of more importance and it is preferred first to calibrate the sample concentration for optimum results. However, calibration is not absolutely necessary and the concentration of the nucleic acid in the sample may be estimated by standard methods.

The calibration procedure will be of particular interest, if it is important to know the exact allele frequencies in a pool, or if the pool consists of a few samples and/or there are large differences in the individual DNA concentrations.

The amount of template nucleic acid from the pool of nucleic acid used for amplification has been found by the inventors under certain circumstances to be important when performing allele frequency studies. In order to obtain reproducible results, at least 10 ng, preferably 10 to 100 ng, more preferably 10 to 50 ng and even more preferably 10 to 20 ng of nucleic acid is generally preferred. Such amounts are particularly recommended for genomic DNA but is equally applicable to cases wherein PCR products are pooled.

Generally speaking the absolute level of signal detected (e.g. peak height in a Pyrogram™), does not significantly affect the accuracy of allele frequency determinations as long as the analysed signals (e.g. peaks) are well above (i.e. distinguishably above) noise level. Generally speaking however, the lowest peak in a Pyrogram™ is ideally at least 2 RLU (relative light units) to distinguish from noise/background. Single peak heights of at least 10 or 15 RLU have generally been found to be reliable, particularly if one of the alleles is represented at a low frequency.

Preferably, the concentration of the nucleic acid in the sample is determined by a primer-extension reaction (as described previously).

Preferably, the genomic nucleic acid from all individuals in the population are pooled, and amplified prior to analysis. Suitable amplification techniques have been discussed previously. As mentioned before, the nucleic acid may be of any suitable nature. In order to increase the accuracy of allele frequency calculations, it is advisable to separate the nucleic acid pool prior to amplification into "sub-pools" (or several PCR replicates) to enable multiple allele-frequency assays of the invention to be performed for the same allele. Preferably, there are 1 or more sub-pools (i.e. 2, 3, 4, 5, 6, 7, 8, 9, 10 or more), and therefore the same study is replicated 1 or more times. As mentioned previously, there is preferably at least 10 ng of nucleic acid present in the pool prior to amplification. Calculating an average allele frequency from the sub-pools improves the accuracy of allele frequency determination when dealing with genomic or amplified nucleic acid material. The use of amplified nucleic acid in the method of the invention is also envisaged. However, less replicate allele frequency experiments need to be performed than if genomic nucleic acid is pooled.

In order for the primer-extension reaction (either for calibration or allele frequency determination) to be performed, the nucleic acid molecule, regardless of whether or not it has been amplified, is conveniently provided in a single-stranded format. The nucleic acid may be subjected to strand separation by any suitable technique known in the art (e.g. Sambrook et al., supra), for example by heating the nucleic acid, or by heating in the presence of a chemical denaturant such as formamide, urea or formaldehyde, or by use of alkali.

However, this is not absolutely necessary and a double-stranded nucleic acid molecule may be used as template, e.g. with a suitable polymerase having strand displacement activity.

Where a preliminary amplification step is used, regardless of how the nucleic acid has been amplified, all components of the amplification reaction need to be removed, to obtain pure nucleic acid, prior to carrying out the typing assay of the invention. For example, unincorporated nucleotides, PCR primers, and salt from a PCR reaction need to be removed. Methods for purifying nucleic aids are well known in the art (Sambrook et al., supra), however a preferred method is to immobilize the nucleic acid molecule, removing the impurities via washing and/or sedimentation techniques.

Optionally, therefore, the target nucleic acid may be provided with a means for immobilization, which may be introduced during amplification, either through the nucleotide bases or the primer/s used to produce the amplified nucleic acid.

To facilitate immobilization, the amplification primers used according to the invention may carry a means for immobilization either directly or indirectly. Thus, for example the primers may carry sequences which are complementary to sequences which can be attached directly or indirectly to an immobilizing support or may carry a moiety suitable for direct or indirect attachment to an immobilizing support through a binding partner.

Numerous suitable supports for immobilization of DNA and methods of attaching nucleotides to them, are well known in the art and widely described in the literature. Thus for example, supports in the form of microtitre plate (MTP) wells, tubes, dipsticks, particles, beads, fibres or capillaries may be used, made for example of agarose, sepharose, cellulose, alginate, cellulose alginate, teflon, latex or polystyrene. Advantageously, the support may comprise beads, e.g. sepharose beads produced by Amersham Biosciences (Uppsala, Sweden), or magnetic particles eg. the superparamagnetic beads produced by Dynal AS (Oslo, Norway) and sold under the trademark DYNABEADS®. Chips may be used as solid supports to provide miniature experimental systems as described for example in Nilsson et al. (Anal. Biochem. (1995), 224:400–408).

The solid support may carry functional groups such as hydroxyl, carboxyl, aldehyde or amino groups for the attachment of the primer or capture oligonucleotide. These may in general be provided by treating the support to provide a surface coating of a polymer carrying one of such functional groups, eg. polyurethane together with a polyglycol to provide hydroxyl groups, or a cellulose derivative to provide hydroxyl groups, a polymer or copolymer of acrylic acid or methacrylic acid to provide carboxyl groups or an amino alkylated polymer to provide amino groups. U.S. Pat. No. 4,654,267 describes the introduction of many such surface coatings. Alternatively, the support may carry other moieties for attachment, such as avidin or streptavidin (binding to biotin on the nucleotide sequence), DNA binding proteins (eg. the lac I repressor protein binding to a lac operator sequence which may be present in the primer or oligonucleotide), or antibodies or antibody fragments (binding to haptens eg. digoxigenin on the nucleotide sequence). The streptavidin/biotin binding system is very commonly used in molecular biology, due to the relative ease with which biotin can be incorporated within nucleotide sequences, and indeed the commercial availability of biotin-labelled nucleotides. This represents one preferred method for immobilisation of target nucleic acid molecules according to the present invention. Streptavidin-coated DYNABEADS® are commercially available from Dynal AS, and streptavidin-coated Sepharose beads are commercially available from Amersham Biosciences.

As mentioned above, immobilization may conveniently take place after amplification. To facilitate post amplification immobilisation, one or both of the amplification primers are provided with means for immobilization. Such means may comprise as discussed above, one of a pair of binding partners, which binds to the corresponding binding partner carried on the support. Suitable means for immobilization thus include biotin, haptens, or DNA sequences (such as the lac operator) binding to DNA binding proteins.

When immobilization of the amplification products is not performed, the products of the amplification reaction may simply be separated by for example, taking them up in a formamide solution (denaturing solution) and separating the products, for example by electrophoresis or by analysis using chip technology. Immobilization provides a ready and simple way to generate a single-stranded template for the extension reaction. As an alternative to immobilization, other methods may be used, for example asymmetric PCR, exonuclease protocols or quick denaturation/annealing protocols on double stranded templates may be used to generate single stranded DNA. Such techniques are well known in the art.

The method of the invention allows the determination of the frequency of an allele in a population (i.e. a group of individuals exhibiting disease or trait, a familial group, an ethnic group, a geographical group), wherein the allele assessed is a single nucleotide polymorphism (SNP) or any other allelic variant.

The method of the present invention is particularly advantageous in determining whether a particular allelic variant is linked to disease or trait. To enable such determination, 2 or more (i.e. 3 OR 4, 5, 6, 7, 8, 9 OR 10) pools of nucleic acid molecules are analyzed. One pool comes from a population exhibiting said disease or trait, whilst the second pool is selected from a population which do not exhibit said disease or trait. If the frequency of one allelic variant is greater in the 'diseased', population, this points towards the allele being associated with the disease or trait. However, it will be appreciated that the method of the invention can be performed on 1 pool in isolation.

The method of the present invention may be used to confirm whether an allelic variation is present in a population. For example, an SNP may be identified in silico (by searching databases and homologues) or identified in one population (i.e. an isolated geographical group or ethnic group), and it may be desirable to ascertain the frequency of an allele in another population (i.e. a different ethnic group or different familial group).

The method of the present invention is particularly advantageous in studies of mutations associated with cancer. In this case, the population is a sample of cells removed from a patient (i.e human, livestock animal, domestic animal or laboratory animal). In the population of cells, there will be a mixture of healthy and diseased cells, and the nucleic acid from all cells in the population will be pooled. The population can then be scanned for SNPs which are associated with diseased state in the patient, giving patient-specific information on the disease-associated allele, and the frequency of that allele in a population of cells. This type of information could be invaluable in the treatment of cancer, by aiding diagnosis and prognosis. Further, knowledge of the allele involved can allow the tailoring of treatment for the allele involved; this technology is known as pharmacogenomics. Repeated testing of a population of cells from an individual can give an estimation of the proportion of cells that are carrying the disease-associated allele. By using the method of the invention, it is possible to separate the mixed genotypes present in the mixed cell populations. This is a great advantage over prior methods where mixed genotypes were indicated due to a mixture of cell types being present. It will be understood that this technology could also be used to analyse multiploid genomes (e.g. plants). A further application of determining allele frequency from a population of cells is that loss of heterozygosity can be examined. This will detect whether a segment of chromosome has been lost in tumour tissue.

A further application of the method of the invention is testing for 'genetic drift'. Using the method of the invention, it will be possible to obtain data on a particular allele frequency within a given population at given time intervals, and determine whether over time, the frequency of an allele changes. This type of analysis will therefore involve taking nucleic acid samples from multiple generations in a population. It is thought that genetic drift is a useful indicator of evolutionary change, and the method of the invention will be able to measure such allele frequency change quickly and simply.

A further application of the method of the invention is for quantification of a gene/allele in human samples for trisomy tests (or other chromosome abnormalities or gene multiplication etc). This is important in different syndromes where one chromosome occurs in three copies instead of two as normal. A well-known syndrome is Downs Syndrome or trisomy-21. Other trisomies are trisomy-13, and 18. Other syndromes related to duplications of sex chromosomes (or other chromosome number abnormality) can also be analysed using the method of the invention. This can be performed by quantifying the number of alleles of any gene (or indeed any particular selected nucleotide sequence containing allelic variation or polymorphism) on the selected chromosome.

The method of the invention is advantageous in that it determines the exact sequence of the SNP or allelic variant, together with a direct measurement of the amount of nucleotide incorporated. The primer extension reaction generates a "pattern" indicative of nucleotide incorporation, correlated to the nucleotide added to the reaction mixture. The pattern is a cumulative picture of nucleotide incorporation for the primers bound to all of the nucleic acid molecules present in the pool. To enable the allele frequency of an SNP or allelic variant in the pool to be determined, several measurements need to be taken, to enable the allele frequency to be calculated. The height of the peak (see before) for each allelic variant residue needs to be measured, which should be present adjacent to each other on the pattern of nucleotide incorporation obtained. The calculation of allele frequency can thus be performed as follows:

$$\text{Allele frequency (Allele 2)} = \frac{\text{Peak Height (allele 2)}}{\text{Peak Height (allele 2)} + \text{Peak Height (allele 1)}} \times 100\%$$

Therefore, if the SNP is C/T the calculation would be performed thus:

$$\text{Allele frequency } T = \frac{\text{Peak height } T}{\text{Peak height } T + \text{Peak height } C} \times 100\%$$

Thus, it is possible to obtain accurate, cost-effective and rapid information on SNP allele frequencies in a population using nucleic acid pooling and primer-extension reactions, by monitoring nucleotide incorporation.

The method of the invention relies upon the knowledge of the location and potential variants of the SNP or allelic variant, together with further known sequence information (e.g. with known sequences of conserved/semi-conserved regions) from which to determine an appropriate primer binding site and design a complementary extension primer. Using the method of the invention, the allele frequency of any SNP or allelic variant may be determined, whether present in coding or non-coding regions.

The invention also comprises kits for carrying out the method of the invention. These will normally include one or more of the following components:

optionally primer(s) for in vitro amplification; a primer for the primer extension reaction; nucleotides for amplification and/or for the primer extension reaction (as described above); a polymerase enzyme for the amplification and/or primer extension reaction; and means for detecting primer extension (e.g. means of detecting the release of pyrophosphate as outlined and defined above).

The invention will now be described by way of nonlimiting examples.

EXAMPLE 1

Templates and Primers

These examples used DNA from 3 different sources which was either extracted from cell lines or from genomic sources. In total, DNA from 122 individual sources was used. The concentration of nucleic acid in some of the samples had been determined previously by measurement of absorbance at a wavelength of 260 nm. These samples were diluted to 2 ng/µl based on the absorbance measurements and the samples were either pooled directly, or after concentration calibration.

Some examples were performed on template oligonucleotides instead of PCR products. These oligonucleotides were obtained from Interactiva Ulm, Germany.

PCR amplification primers and sequencing primers were designed using Oligo 6.0 (Med Probe AS, Oslo, Norway). All primers were ordered from Interactiva (Supra).

TABLE 1

Primers and SNP definitions

| SNP_ID | Upstream primer | Downstream primer | Sequencing primer | Fragment length [bp] | Sequencing output |
|---|---|---|---|---|---|
| Eu1 (ACP-240) | E1a (SEQ ID NO: 3) 5'-Biotin-ggt cgg gct ggg aag at-3' | E1b (SEQ ID NO: 4) 5'-gct ccc gca gag gaa gc-3' | E1s (SEQ ID NO: 5) 5'-aga aag ggc ctc ctc tct tt-3' | 158 | A/T |
| Eu4 (ACEex 15) | E4a (SEQ ID NO: 6) 5'-gcc agg aag ttt gat gtg aac-3' | E4b (SEQ ID NO: 7) 5'-Biotin-gat tcc cct ctc cct gta cct-3' | E4s (SEQ ID NO: 8) 5'-gac cta gaa cgg gca gc 3' | 145 | A/G |
| Eu7 (ANP1218) | E7a (SEQ ID NO: 9) 5'-Biotin-tga tgt aac cct cct ctc ca3' | E7b (SEQ ID NO: 10) 5'-cgg ctt acc ttc tgc tgt agt-3' | E7s (SEQ ID NO: 11) 5'-acg gca gct tct tcc cc-3' | 142 | C/T |
| 460R | PSO 145 (SEQ ID NO: 12) 5'-B-ggc tgc tgt tct gaa acc atc tga -3' | PSO 146 (SEQ ID NO: 13) 5'-ttc agg aac gcg ggc aag tc -3' | PSO 147 (SEQ ID NO: 14) 5'-gag cag tcc cca ccc -3' | 101 | CC/T |
| 461R | Same as 460R | Same as 460R | PSO 148 (SEQ ID NO: 15) 5'-gcg ggc aag tcc aat -3' | Same as 460R | C/TT |
| 465R | PSO 149 (SEQ ID NO: 16) 5'-B-gga aca ctg cct ccc act ttc tt-3' | PSO 150 (SEQ ID NO: 17) 5'-tcc cca tgc agc cct aga gac-3' | PSO 151 (SEQ ID NO: 18) 5'-gga gaa gtc cag tgt gc -3' | 85 | C/T |
| 466F | PSO 182 (SEQ ID NO: 19) 5'-ttc caa agg acg cga cca taa-3 | PSO 183 (SEQ ID NO: 20) 5'-B-cct gca ccc cag acc act ga-3' | PSO 184 (SEQ ID NO: 21) 5'-tag ctg cgc ggg aa -3' | 111 | C/T/G |
| 470R | PSO 155 (SEQ ID NO: 22) 5'-B-cct acc cac agg cca gaa-3' | PSO 156 (SEQ ID NO: 23) 5'-gcc tgg gac ctc act gtc -3' | PSO 157 (SEQ ID NO: 24) 5'-gga gac aga atg ctg at -3' | 102 | C/A |
| 471F | PSO 158 (SEQ ID NO: 25) 5'-gtt gcc ctc tgg ttc cac ct -3' | PSO 159 (SEQ ID NO: 26) 5'-B-tgt ctc cag cag ctc ctt cat c -3' | PSO 160 (SEQ ID NO: 27) 5'-gcc cag gaa gga ac -3' | 126 | CCC/T |

TABLE 1-continued

Primers and SNP definitions

| SNP_ID | Upstream primer | Downstream primer | Sequencing primer | Fragment length [bp] | Sequencing output |
|---|---|---|---|---|---|
| 481R | PSO 167 (SEQ ID NO: 28) 5'-B-gat gct gta aca gag acc cca ta -3' | PSO 168 (SEQ ID NO: 29) 5'-ctg gga tta cag gtg tga aca ct -3' | PSO 169 (SEQ ID NO: 30) 5'-tag gag caa gaa gta aac -3' | 110 | T/G |
| 486R | PSO 173 (SEQ ID NO: 31) 5'-B-caa ggt aga gaa gtg cag cat tca -3' | P50 174 (SEQ ID NO: 32) 5'-ttg att ctc ttt gag ccc aga tgt -3' | PSO 175 (SEQ ID NO: 33) 5'-gcc tgg agc tgt taa t -3' | 115 | TT/C |
| 1000F | PSO 194 | PSO 195 | PSO 196 | 159 | CC/T |
| 3345F | PSO 199 | PSO 200 | PSO 201 | 120 | A/GGGG |

TABLE 2

Oligonucleotides used to create "artificial" SNPs.

| SNP name | Oligoname | Oligo Sequence | Sequencing output |
|---|---|---|---|
| Oligo 1 | PSO43SNP | AGTCATGGTGCTGGGGCACTG GCCGTCGTTTTACAACG (SEQ ID NO: 34) | CCCC/T |
|  | PSO44SNP | AGTCATGGTGCTAGGGCAGTG GCCGTCGTTTTTACAACG (SEQ ID NO: 35) |  |
| Oligo 2 | PSO44SNP | AGTCATGGTGCTGGGGGCACT GGCCGTCGTTTTACAACG (SEQ ID NO: 36) | CCCCC/T |
|  | PSO45SNP | AGTCATGGTGCTAGGGGCACT GGCCGTCGTTTTACAACG (SEQ ID NO: 37) |  |
| Oligo 3 | PSO53SNP | AGTCATGGTGCTAAGGGGGCA CTGGCCGTCGTTTTACAACG (SEQ ID NO: 38) | CCCCC/ TTT |
|  | PSO54SNP | AGTCATGGTGCTAAAGGGGCA CTGGCCGTCGTTTTACAACG (SEQ ID NO: 39) |  |
| Sequencing primer | PSO55NUSPT | CGT TGT AAA ACG ACG GC (SEQ ID NO: 40) |  |

PCR Amplification

All fragments in the examples were amplified with the AmpliTaq Gold Kit (Applied Biosystems) and 2 mm MgCl$_2$, according to the following protocol:

| PCR mix | 1 x mix [µl] |
|---|---|
| GeneAmp 10xPCR butter II | 5 |
| MgCl$_2$ (25 mM) | 4 |
| DNTP (2.5 mM) | 2.5 |
| DMSO | 0 |
| Primer a (10 µM) | 1 |
| Primer b (10 µM) | 1 |
| TaqGold (5 U/µl) | 0.3 |
| H$_2$O | 31.2 |
| Sum | 45 |

Approximately 10 ng genomic DNA was added to 45 µl of PCR mix to make a total PCR volume of 50 µl. The PCR cycling conditions were as follows: 95 C for 5 minutes, 45 cycles of (95 C for 15 seconds, Ta C for 30 seconds, 72 C for 15 seconds), 72 C for 5 minutes, 4 C. For SNPs Eu1, Eu4 and Eu7 Ta=57 C. Otherwise Ta=60 C.

EXAMPLE 2

DNA Calibration

In order to calibrate the amount of DNA in each of the samples, an SNP was chosen for analysis. SNP 465R was chosen, it is a C/T SNP that generates good signals without preferential amplification, is not present in a homopolymeric stretch and gives no background signals or uneven peak heights. All samples were genotyped for the chosen SNP.

TABLE 3

Primers used to amplify and sequence SNP 465R.

| SNP ID | Upstream primer | Downstream primer | Sequencing primer | Fragment length | Sequencing SNP output |
|---|---|---|---|---|---|
| 465R | 5-B-gga aca ctg cct ccc act ttc tt-3' (SEQ ID NO: 16) | 5-tcc cca tgc agc cct aga gac-3 (SEQ ID NO: 17) | 5-gga gaa gtc cag tgt gc-3 (SEQ ID NO: 18) | 85 | G/AC/T |

The genotyping was performed as follows. 5 μl genomic DNA (at a concentration of approximately 2 ng/μl) was amplified as described previously in Example 1. 25 μl of the PCR product was mixed with 8 μl magnetic beads Dynabeads® (Dynal Biotech ASA, Oslo, Norway) (10 μg/μl) and 17 μl 2×BW buffer (10 mm Tris-HCl, 2M NaCl, 1 mM EDTA, 0.1% Tween 20). The strands were then separated using 50 μl 0.5M NaOH. The sample was then treated with 1× annealing buffer (20 mM Tris-acetate, 5 mM MgAc), and washed. The beads were transferred to a PSQ 96™ plate (Pyrosequencing AB, Uppsala, Sweden) which contained 40 μl of 1× annealing buffer and 5 μl sequencing primer. A sequencing reaction was then performed on a PSQ 96™ instrument (Pyrosequencing AB) using SNP reagent kit, product number 40-0001 (Pyrosequencing AB). Once the genotype of SNP 465R of each sample had been established, calibration was performed.

2.5 μl of sample genomic DNA (at an approximate concentration of 2 ng/μl) was added to 2.5 μl reference genomic DNA and 45 μl PCR mix added, and PCR performed (supra).

The SNP was then analysed (as for genotyping assay) on a PSQ 96™ instrument (Pyrosequencing AB) using Pyrosequencing™ reagents (product no 40-0001).

Calculations and data:
Reference #1: T/T
Reference #2: C/C
Conc (Reference #2)=$X_{Ref\ \#2}\times$ Conc (Reference #1)
Conc (sample)=X×Conc (Reference #1)
Calculation of $X_{Ref\ \#2}$ and $Y_{Ref\ \#2}$:
Reference #2+Reference #1 are pooled:

$$X_{Ref\ \#2} = \frac{\text{Peak height } C}{\text{Peak height } T}$$

$$Y_{Ref\ \#2} = \frac{\text{Peak height } C}{(\text{Peak height } T + \text{Peak height } C)}$$

Calculation of X and Y for all other samples:
Homozygotes C/C sample+Reference #1 are pooled:

$$X = \frac{\text{Peak height } C}{\text{Peak height } T}$$

$$Y = \frac{\text{Peak height } C}{(\text{Peak height } T + \text{Peak height } C)}$$

Homozygote T/T sample+Reference #2 are pooled:

$$X = X_{Ref\ \#2} = \frac{\text{Peak height } T}{\text{Peak height } C} \quad Y = \frac{\text{Peak height } T}{(\text{Peak height } T + \text{Peak height } C)}$$

Heterozygote C/T+Reference #1:

$$X = \frac{2\times\text{Peak height } C}{(\text{Peak height } T - \text{Peak height } C)}$$

$$Y = \frac{\text{Peak height } C}{(\text{Peak height } T + \text{Peak height } C)}$$

TABLE 4

Results for some of the calibrated samples.

| Sample | Sample Genotype | Sample mix | Allele | Peak height | Y | X |
|---|---|---|---|---|---|---|
| Ref #2 | C/C | ref #2 + ref #1 | C | 26.25 | 0.51 | 1.0 |
|  |  |  | T | 25.62 |  |  |
| #1 | C/C | #1 + ref #1 | C | 19.68 | 0.40 | 0.7 |
|  |  |  | T | 30.07 |  |  |
| #2 | C/T | #2 + ref #1 | C | 12.65 | 0.24 | 0.9 |
|  |  |  | T | 41.09 |  |  |
| #3 | C/T | #3 + ref #1 | C | 12.64 | 0.24 | 1.0 |
|  |  |  | T | 39.09 |  |  |
| #18 | T/T | #18 + ref #2 | C | 28.05 | 0.45 | 0.8 |
|  |  |  | T | 23.05 |  |  |
| #19 | T/T | #19 + ref #2 | C | 33.78 | 0.35 | 0.5 |
|  |  |  | T | 18.13 |  |  |

Thus, for further experiments, a given volume of reference #1 is put into the pool, and the X and Y values obtained for the samples can be used to determine the volume of each sample to be added to the pool.

$$\text{Volume (Sample \#1)} = \frac{\text{Volume } (Ref\ \#1)}{X\ (\text{Sample \#1})}$$

$$\text{Volume (Sample \#19)} = \frac{\text{Volume } (Ref\ \#1)}{X\ (\text{Sample \#19})}$$

TABLE 5

Calculated X and Y values and thus volume of sample to use in pooling nucleic acid samples

| Sample | Sample Genotype | Sample mix | Allele | Peak height | Y | X | Volume (μl) |
|---|---|---|---|---|---|---|---|
| Ref #1 | C/C | — | C | — | — | 1.00 | 50 |
|  |  |  | T | — | — |  |  |
| Ref #2 | C/C | ref #2 + ref #1 | C | 26.25 | 0.51 | 1.02 | 49 |
|  |  |  | T | 25.62 |  |  |  |
| #1 | C/C | #1 + ref #1 | C | 19.68 | 0.40 | 0.65 | 76 |
|  |  |  | T | 30.07 |  |  |  |
| #2 | C/T | #2 + ref #1 | C | 12.65 | 0.24 | 0.90 | 56 |
|  |  |  | T | 41.09 |  |  |  |
| #3 | C/T | #3 + ref #1 | C | 12.64 | 0.24 | 0.96 | 52 |
|  |  |  | T | 39.09 |  |  |  |

TABLE 5-continued

Calculated X and Y values and thus volume of sample to use in pooling nucleic acid samples

| Sample | Sample Genotype | Sample mix | Allele | Peak height | Y | X | Volume (µl) |
|---|---|---|---|---|---|---|---|
| #18 | T/T | #18 + ref #2 | C | 28.05 | 0.45 | 0.84 | 59 |
|  |  |  | T | 23.05 |  |  |  |
| #19 | T/T | #19 + ref #2 | C | 33.78 | 0.35 | 0.55 | 91 |
|  |  |  | T | 18.13 |  |  |  |

Assessing DNA Calibration 20 samples were chosen. The DNA concentrations had been determined by using UV absorbance measurements and diluted to a concentration of 2 ng/µl. The 20 samples had been individually genotyped for the SNP (465R) using PSQ™ 96 system. The samples were pooled individually with a "reference DNA", also from the diversity panel. PCR was performed to amplify the fragment containing SNP 465R, and sequencing was performed on PSQ™ 96 system. The concentrations were compared with each other by calculations on the peak heights, and are tabulated in Table 6, below. Further, two test pools were made (one constructed using the calibrated concentrations (pool 1) and one using the original concentrations from UV absorbance measurements (pool 2).

TABLE 6

Calculations for DNA concentration adjustment

| Sample | Sample Genotype | Sample mix | Allele | Peak height | Y | X | Z | Volume (µl) |
|---|---|---|---|---|---|---|---|---|
| Ref #2 | C/C | ref #2 + ref #1 | C | 11,77 | 0,60 | 1,5 | 1,0 | 15 |
|  |  |  | T | 7,79 |  |  |  |  |
| #1 | C/T | #1 + ref #1 | C | 7,17 | 0,34 | 2,2 | 1,5 | 10 |
|  |  |  | T | 13,63 |  |  |  |  |
| #2 | C/T | #2 + ref #1 | C | 7,39 | 0,35 | 2,4 | ,16 | 9 |
|  |  |  | T | 13,44 |  |  |  |  |
| #3 | C/C | #3 + ref #1 | C | 11,42 | 0,60 | 1,5 | 1,0 | 15 |
|  |  |  | T | 7,72 |  |  |  |  |
| #4 | C/T | #4 + ref #1 | C | 6,77 | 0,37 | 2,9 | 1,9 | 8 |
|  |  |  | T | 11,5 |  |  |  |  |
| #5 | C/T | #5 + ref #1 | C | 8,4 | 0,41 | 4,5 | 3,0 | 5 |
|  |  |  | T | 12,13 |  |  |  |  |
| #6 | C/C | #6 + ref #1 | C | 9,02 | 0,52 | 1,1 | 0,7 | 21 |
|  |  |  | T | 8,39 |  |  |  |  |
| #7 | C/T | #7 + ref #1 | C | 8,14 | 0,38 | 3,0 | 2,0 | 7 |
|  |  |  | T | 13,52 |  |  |  |  |
| #8 | C/T | #8 + ref #1 | C | 8,47 | 0,42 | 5,2 | 3,5 | 4 |
|  |  |  | T | 11,71 |  |  |  |  |
| #9 | C/T | #9 + ref #1 | C | 8,02 | 0,39 | 3,5 | 2,3 | 6 |
|  |  |  | T | 12,61 |  |  |  |  |
| #10 | C/T | #10 + ref #1 | C | 6,71 | 0,29 | 1,4 | 0,9 | 16 |
|  |  |  | T | 16,17 |  |  |  |  |
| #11 | C/T | #11 + ref #1 | C | 6,25 | 0,30 | 1,5 | 1,0 | 15 |
|  |  |  | T | 14,44 |  |  |  |  |
| #12 | C/C | #12 + ref #1 | C | 14,2 | 0,66 | 1,9 | 1,3 | 12 |
|  |  |  | T | 7,39 |  |  |  |  |
| #13 | C/T | #13 + ref #1 | C | 7,84 | 0,37 | 2,9 | 1,9 | 8 |
|  |  |  | T | 13,21 |  |  |  |  |
| #14 | C/T | #14 + ref #1 | C | 6,67 | 0,36 | 2,7 | 1,8 | 8 |
|  |  |  | T | 11,63 |  |  |  |  |
| #15 | C/T | #15 + ref #1 | C | 3,08 | 0,20 | 0,7 | 0,4 | 34 |
|  |  |  | T | 12,31 |  |  |  |  |
| #16 | C/C | #16 + ref #1 | C | 11,82 | 0,56 | 1,3 | 0,8 | 18 |
|  |  |  | T | 9,29 |  |  |  |  |
| #17 | C/C | #17 + ref #1 | C | 15,91 | 0,73 | 2,7 | 1,8 | 8 |
|  |  |  | T | 5,96 |  |  |  |  |
| #18 | T/T | #18 + ref #2 | C | 12,91 | 0,42 | 0,7 | 0,7 | 21 |
|  |  |  | T | 9,41 |  |  |  |  |
| #19 | T/T | #19 + ref #2 | C | 11,52 | 0,44 | 0,8 | 0,8 | 19 |
|  |  |  | T | 8,88 |  |  |  |  |

According to previous calculations for SNP465R observed differences in DNA concentrations would not have had any detectable impact on the allele frequency measurement for 465R in these pools. Expected allele frequency for the T-allele was 40% in pool 1 and 41% in pool 2, which is an undetectable difference. Therefore, two further SNPs were selected to test the pools, SNP 461R and 470R. The difference between the two pools was expected to be 3% for both SNPs and that is a detectable difference.

Figure 1:
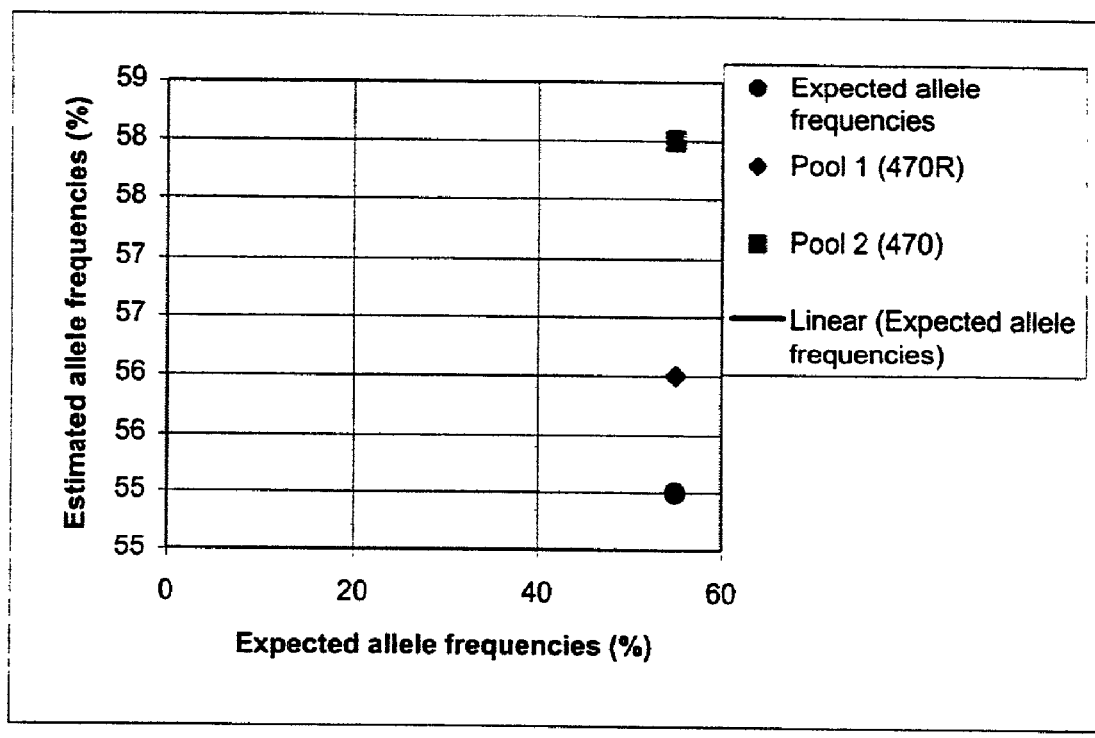
FIG. 1a depicts the expected allele frequency (SNP 470R) and calculated allele frequency determined (estimated) via Pyrosequencing™. The results are plotted as estimated allele frequency versus expected allele frequency. Pool 1 has been calibrated according to Example 3, whereas the DNA concentration in pool 2 has been assayed via absorbance of light at 260 nm.
FIG. 1b depicts the expected allele frequency (SNP 461R) and calculated allele frequency determined (estimated) via Pyrosequencing™. The results are plotted as estimated allele frequency versus expected allele frequency. Pool 1 has been calibrated according to Example 3, whereas the DNA concentration in pool 2 has been assayed via absorbance of light at 260 nm. It should be noted that SNP 461R consistently gives a peak that is 3% too high, and the results shown are consistent with this.
Figure 1:
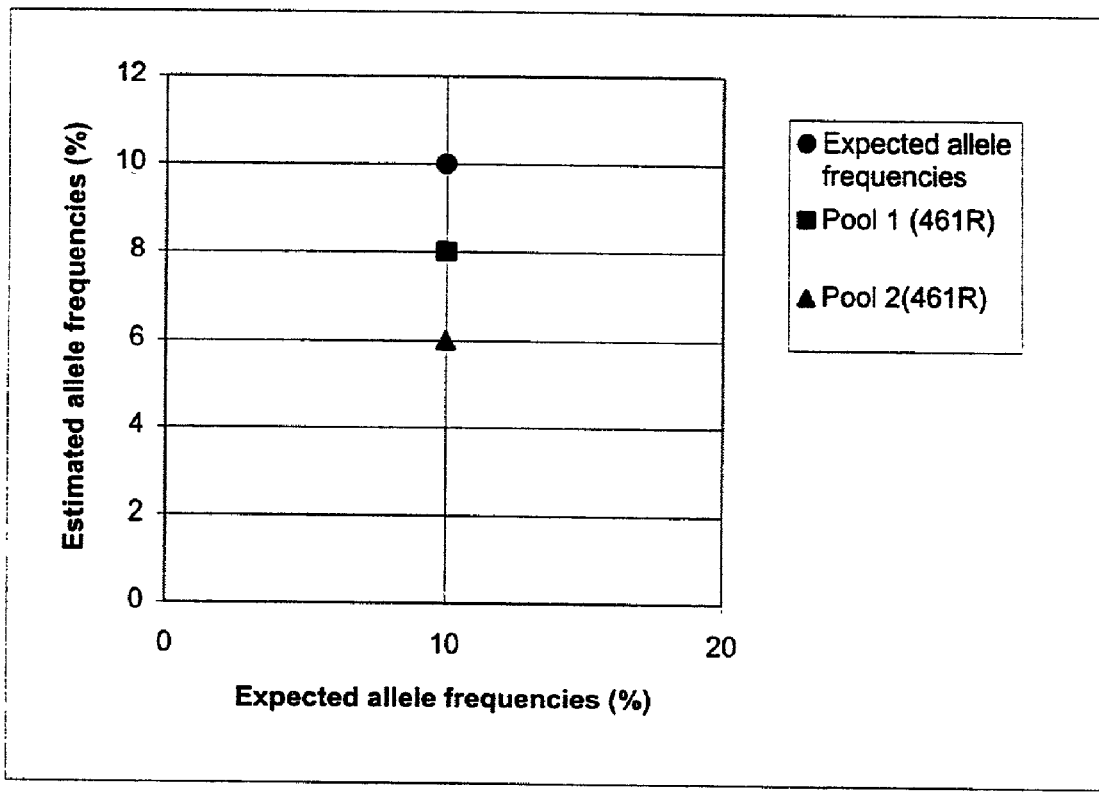

For both pools, the estimated allele frequencies were in good accordance with what was expected, see FIG. 1 and Table 7. The experiment showed that it is possible to use Pyrosequencing™ as a method to calibrate DNA concentrations before pooling DNA. Further, the calibrated pool was more in accordance with the theoretical frequencies, as determined from individual genotypes (10% for 461R and 55% for 470R).

TABLE 7

Measured allele frequencies and STD for each pool compared to the theoretically calculated frequencies of the DNA pools.

|  | 461R Pool 1 | 461R Pool 2 | 470R Pool 1 | 470R Pool 2 |
| --- | --- | --- | --- | --- |
| Replicate 1 | 8.5 | 5.9 | 64.7 | 56.9 |
| Replicate 2 | 6.1 | 7.2 | 55.8 | 54.1 |
| Replicate 3 | 6.6 | 8.1 | 59.3 | 58.1 |
| Replicate 4 | 9.3 | 4.8 | 51.6 | 59.8 |
| Replicate 5 | 8.3 | 3.5 | 55.3 | 56.5 |
| Replicate 6 | 6.7 | 5.6 | 56.1 | 59.2 |
| Replicate 7 | 10.2 | 4.7 | 54.3 | 62.8 |
| Replicate 8 | 7.1 | 6.6 | 57.1 | 58.5 |
| Replicate 9 | 6.6 | 6.3 | 55.2 | 54.7 |
| Replicate 10 | 6.9 | 3.8 | 57.4 | 55.5 |
| average | 7.6 | 5.6 | 56.8 | 57.6 |
| calculated | 10.0 | 7.0 | 55.0 | 58.0 |
| STD | 1.3 | 1.3 | 3.5 | 2.5 |

Therefore, this method of sequencing can also be used reliably for the calibration of relative concentrations in a pool of nucleic acid. This has applications for all sequencing-by-synthesis protocols.

EXAMPLE 3

SNP Analysis Protocol

The pooled DNA (calibrated according to Example 2, or of known concentration) was added to 45 µl PCR mix (supra) and amplified as described previously. 25 µl of the PCR product was mixed with 8 µl magnetic beads—Dynabeads® (Dynal Biotech ASA, Oslo, Norway) (10 µg/µl) as described in Example 2. Annealing of the primer to the template DNA was performed with 15 pmol sequencing primer, for 2 minutes at 80 C. The samples were allowed to cool to room temperature and the primer extension reaction was performed on a PSQ™ 96 instrument (Pyrosequencing AB) using SNP reagent kit (Pyrosequencing AB). Once the peak height data was collected for the DNA pool, the allele frequency can be calculated as follows if the SNP is not present in a homopolymeric stretch:—

Allele frequency (Allele 2)=

$$\frac{\text{Peak Height (Allele 2)}}{\text{Peak Height (Allele 2)} + \text{Peak Height (Allele 1)}} \times 100\%$$

EXAMPLE 4

Pooling Strategies

It is important to determine whether it is more preferable to pool genomic DNA or PCR product, as experimental variance can be expected once PCR amplification of the genomic DNA has been performed. Thus, the SNP Eu7 (A/G) was investigated, by sequencing the SNP in reverse (T/C).

Ninety samples were individually genotyped for Eu7 and thereafter pooled either before or after PCR amplification, with five replicate reactions performed for each pool. The expected allele frequency is 27% G. The experiment was repeated in 3 subset populations (30–40 samples out of the 90) with lower allele frequencies (15% G, 10% G and 5% G, respectively).

Each replicate of a genomic DNA- or PCR-pool, 40 µl PCR product was incubated with 15 µl magnetic beads (10 µg/µl) and 25 µl 2×BW buffer. The resulting single-peak height levels were about 40–60 RLU. The theoretical allele frequency values (determined from the individual sample genotypes) in the four tested sample sets were 27% G, 15% G, 10% G, and 5% G respectively.

Pooling of PCR products resulted in good estimates of allele frequencies in all four pools (26%, 17%, 11%, and 7% respectively), and with low variance between replicate sequencing reactions. Pooling of genomic DNA resulted in accurate results (28%, 17%, 12%, and 6% respectively), but with slightly larger variation between replicate pools.

The experiment indicated that pooling of genomic DNA is possible with the same accuracy as can be obtained with pooled PCR products. However, the replicate PCR amplifications on the genomic DNA pool introduces additional experimental variance. Pooling of genomic DNA may therefore require testing more replicate pools to obtain the same accuracy as when pooling PCR products.

It can also be concluded that 5% of the G-allele could be reliably detected showing that even low allele frequencies are capable of measurement using the method of the invention.

Figure 2A:
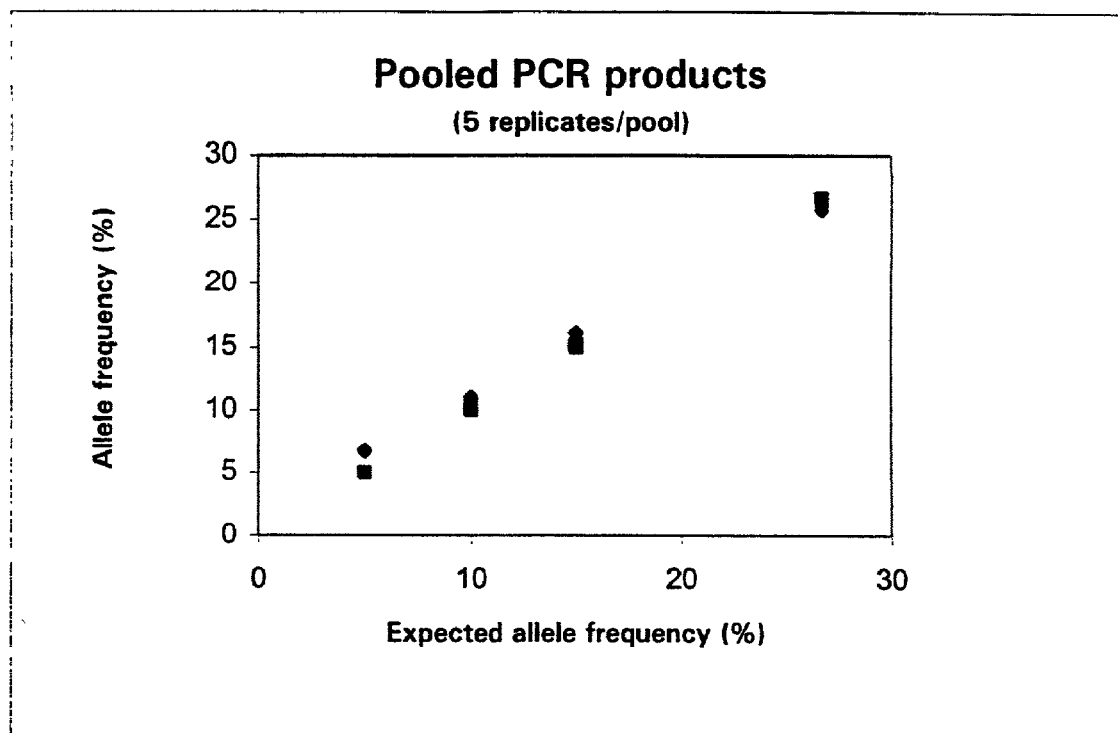
FIG. 2a depicts the calculated allele frequency results of 4 pools of PCR products determined via Pyrosequencing™. 5 replicate reactions were performed on each pool. The results are plotted as estimated allele frequency versus expected allele frequency, both in percentage (%). The pools contained 27% G, 15% G, 10% G and 5% G. The calculated allele frequency value (shown as diamonds) are in close correlation to the expected values (shown as squares).
Figure 2B:
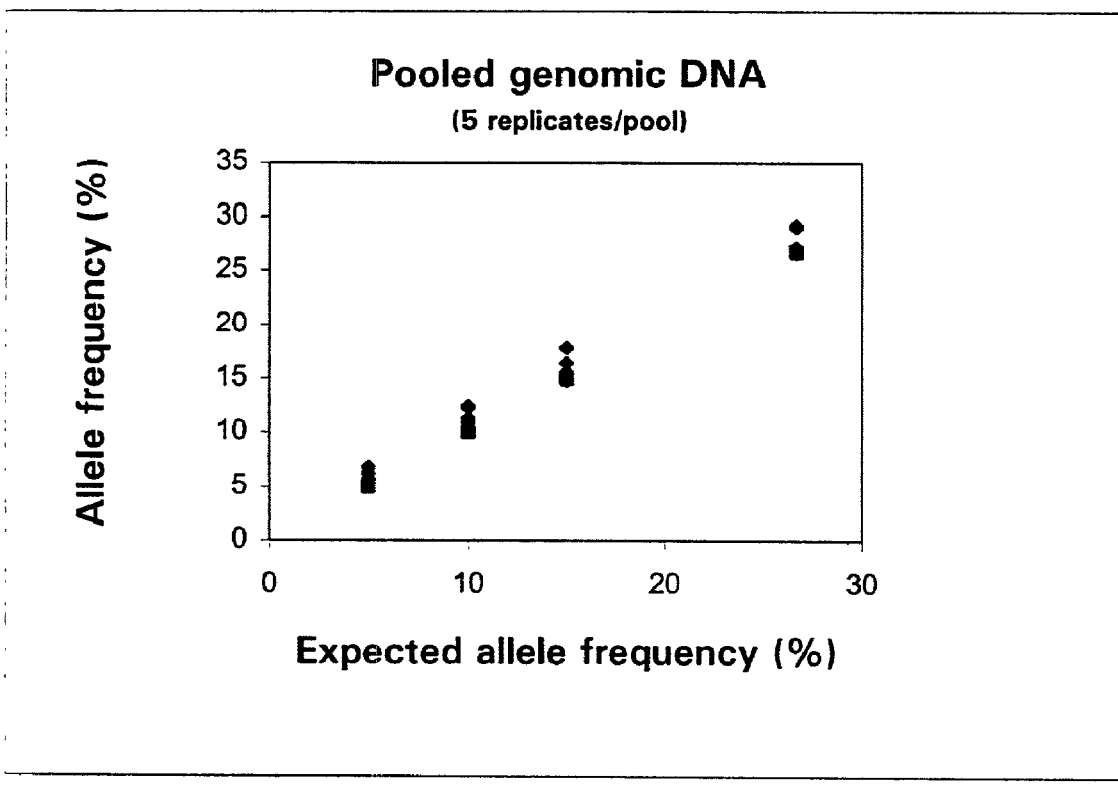
FIG. 2b depicts the calculated allele frequency results of 4 pools of genomic DNA samples determined via Pyrosequencing™. 5 replicate reactions were performed on each pool. The results are plotted as estimated allele frequency versus expected allele frequency, both in percentage (%). The pools contained 27% G, 15% G, 10% G and 5% G. The calculated allele frequency value (shown as diamonds) are in close correlation to the expected values (shown as squares).
Figure 3A:
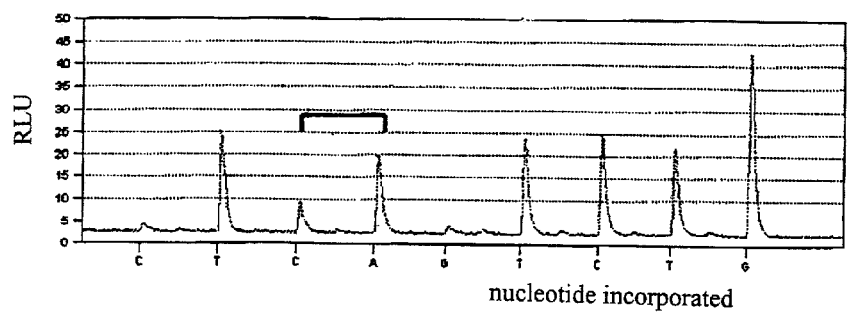
FIG. 3a shows DNA sequencing on pooled genomic DNA over SNP 470R, the expected sequence of which is T[C/A]TCTGG. 40 µl PCR product was incubated with 15 µl magnetic beads (10 µg/µl) and 25 µl 2×BW buffer. Pyrosequencing™ was then performed on a PSQ™ 96 system instrument using Pyrosequencing™ SNP reagent kit. The peak heights were measured in order to calculate the frequency of the allele. The results are shown generally as nucleotide incorporated (i.e. A, C, G or T) versus amount of light released (in RLU). The 2 nucleotide incorporations which relate to the SNP are marked. The experimental conditions are as described in Example 4.
Figure 3B:
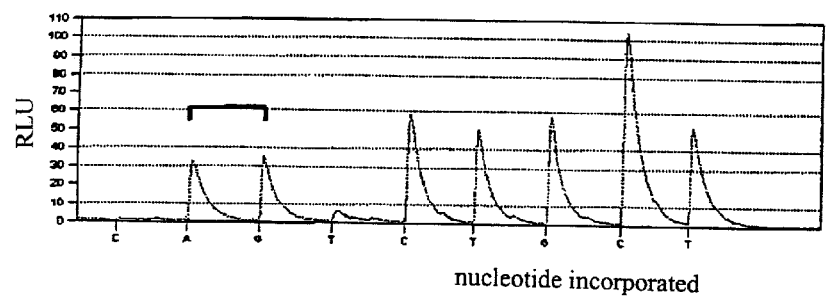
FIG. 3b shows DNA sequencing on pooled genomic DNA over SNP EU4, the expected sequence of which is [A/G]CTGCCT. 40 µl PCR product was incubated with 15 µl magnetic beads (10 µg/µl) and 25 µl 2×BW buffer. Pyrosequencing™ was then performed on a PSQ™ 96 system instrument using Pyrosequencing™ SNP reagent kit. The peak heights were measured in order to calculate the frequency of the allele. The results are shown generally as nucleotide incorporated (i.e. A, C, G or T) versus amount of light released (in RLU). The 2 nucleotide incorporations which relate to the SNP are marked. The experimental conditions are as described in Example 4.
Figure 3C:
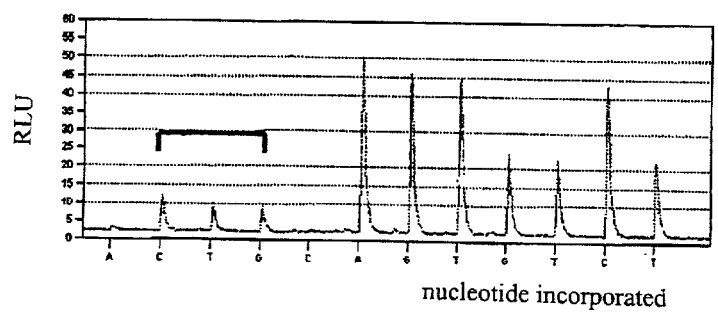
FIG. 3c shows DNA sequencing on pooled genomic DNA, over SNP 466F, the sequence of the nucleic acid should be [C/T/G]AAGGTTGTCCT (SEQ. ID NO: 1) 40 µl PCR product was incubated with 15 µl magnetic beads (10µg/µl) and 25 µl 2×BW buffer. Pyrosequencing™ was then performed on a PSQ™ 96 system instrument using Pyrosequencing™ SNP reagent kit. The peak heights were measured in order to calculate the frequency of the allele. The results are shown generally as nucleotide incorporated (i.e. A, C, G or T) versus amount of light released (in RLU). The 3 nucleotide incorporations which relate to the SNP are marked. The experimental conditions are as described in Example 4.
Figure 3D:
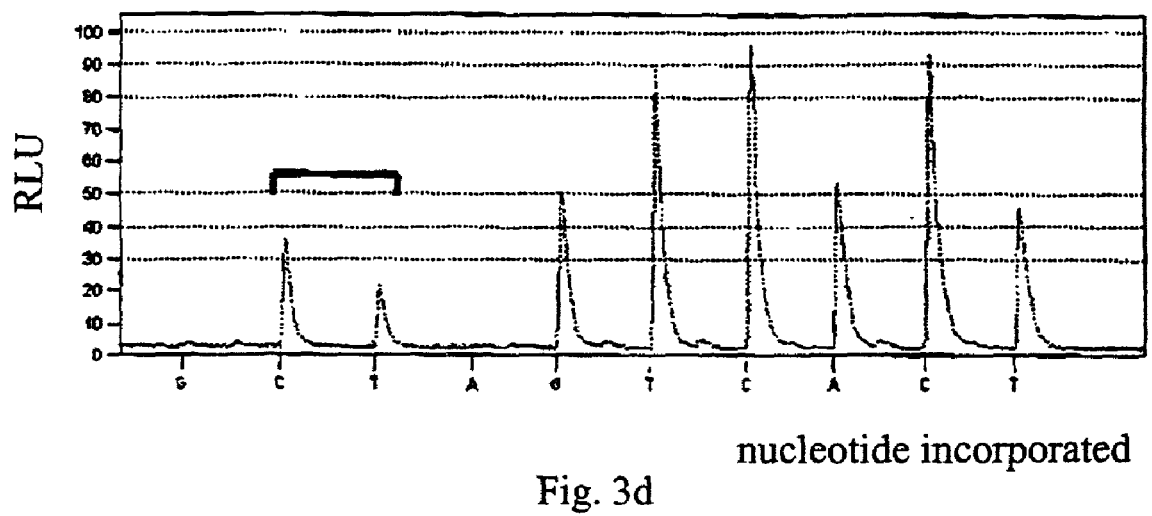
FIG. 3d shows DNA sequencing on pooled genomic DNA, over SNP 465R, the sequence of the nucleic acid should be [CIT]GTTCCACCT (SEQ. ID NO: 2). 40 µl PCR product was incubated with 15 µl magnetic beads (10 µg/µl) and 25 µl 2×BW buffer. Pyrosequencing™ was then performed on a PSQ™ 96 system instrument using Pyrosequencing™ SNP reagent kit. The peak heights were measured in order to calculate the frequency of the allele. The results are shown generally as nucleotide incorporated (i.e. A, C, G or T) versus amount of light released (in RLU). The 2 nucleotide incorporations which relate to the SNP are marked. The experimental conditions are as described in Example 4.
Figure 3E:
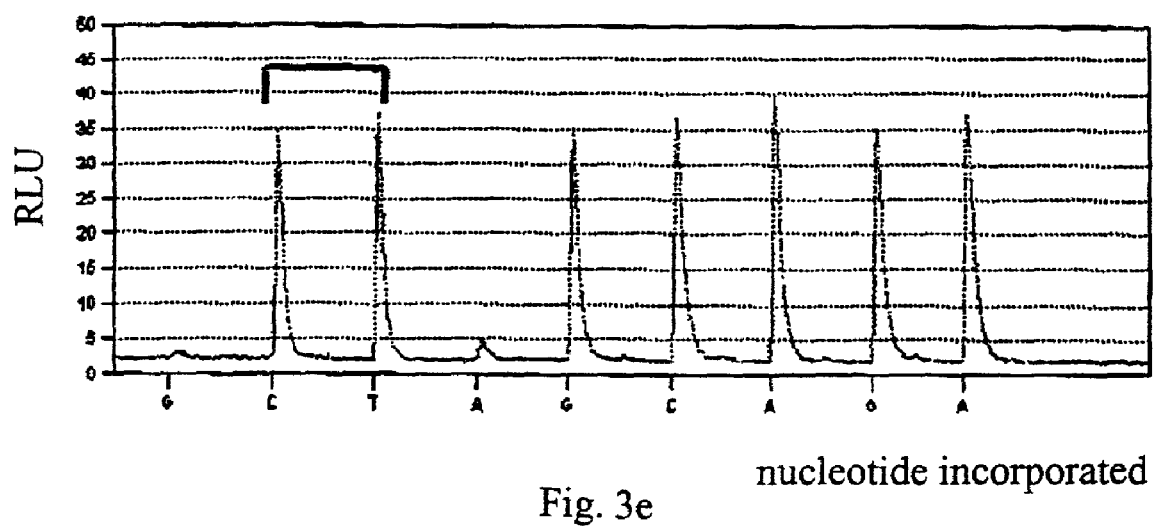
FIG. 3e shows DNA sequencing on pooled genomic DNA, over SNP 461R, the sequence of the nucleic acid should be [C/T]TGCAGA. 40 µl PCR product was incubated with 15 µl magnetic beads (10 µg/µl) and 25 µl 2×BW buffer. Pyrosequencing™ was then performed on a PSQ™

FIG. 2a represents graphically the allele frequency results for 5 replicate PCR products on each of 4 pools. It can be seen that the estimated allele frequency (%) is in close correlation with the measured frequency. FIG. 2b shows graphically the allele frequency results for pooled genomic DNA, 5 replicate reaction per pool. Although the measured allele frequency is slightly more variable for the genomic DNA when compared to the PCR products, the calculated mean values were still in close agreement with the estimated frequency.

Pooling of Genomic DNA

Ninety samples were individually genotyped for five different SNPs. One A/G-SNP (Eu4), one tri-allelic SNP (466F), one simple C/T-SNP (465R), one C/T-SNP followed by a T (461R), and one A/C-SNP (470R). A pool containing ninety genomic DNA samples was created without calibration of the DNA concentrations and therefore differed slightly in individual DNA concentrations. For Eu4, five replicate PCR reactions were performed. For the other four SNPs, ten replicate PCR reactions were used. All PCR amplifications were performed with 10 ng genomic DNA as starting material in the PCR reaction. For Eu4, 40 µl PCR product was used for sequencing. For the other four SNP assays, 30 µl of each PCR product was used for Sequencing. The average allele frequencies and standard deviations were calculated.

Results on allele frequencies were calculated for five different SNPs, the results for which are tabulated below:

TABLE 8

Results from pooling experiments

| SNP | Sequence | Expected Frequency | Measured Frequency |
|---|---|---|---|
| 466F | [C/T/G]AAGGTTGTCCT (SEQ ID NO: 1) | C 38.1% <br> T 37.5% <br> G 24.4% | C 40.8% <br> T 32.1% <br> G 27.1% |
| 465R | [C/T]GTTCCACCT (SEQ ID NO: 2) | C 64.4% <br> T 35.6% | C 65.1% <br> T 34.9% |
| 461R | [C/T]TGCAGA | C 92.2% <br> T 7.8% | C 96.5% <br> T 3.5% |
| 470R | T[C/A]TCTGG | C 28.9% <br> A 71.1% | C 28.2% <br> C 71.8% |
| Eu4 | [A/G]CTGCCT | G 56.7% <br> A 43.3% | G 56.0% <br> A 44.0% |

The sequencing results are shown as "pyrograms"™ (FIGS. 3a, 3b, 3c, 3d and 3e), wherein the peak height resulting from nucleotide addition is measured. No concentration calibration was performed for this experiment, and therefore different amounts of the individual nucleic acid samples were added to the pool. In view of this, the results are remarkably close to the estimated allele frequency for each pool. The standard deviation values for the results were between 0.8 and 1.8, which was found to be comparable with previous allele frequency experiments.

The result for the SNP 461R, which contains a T residue in a stretch of 2 T residues showed a lower value than expected. From further experimentation, this result turned out to be consistent for this allele, probably due to the fact that the SNP was present in a homopolymeric stretch.

The pyrogram™ for SNP Eu4 (FIG. 3e) shows very high and wide peaks. This was due to the use of 40 µl of PCR product.

Detecting Allele Frequency Differences Between Pools

Four sample pools, composed of 39–90 genomic DNA samples were constructed for both SNP 465R and SNP 461R. DNA concentration calibration was not performed before pooling. Allele frequencies were measured for 10 replicate reactions of each pool. 10 ng genomic DNA was used in a 50 µl PCR reaction and 30 µl of the PCR product was used for the primer extension reactions. The average allele frequencies and standard deviations were calculated. 95% and 99% confidence intervals were also estimated for the measured allele frequencies.

As previously observed, the measured frequencies for the T-allele of SNP 461R are too low. However, the deviation proved to be consistent, enabling detection of even small differences in allele frequencies between pools. The smallest sample pool, SNP465R:4 with 39 samples, showed the largest deviation from the expected frequency, indicating the importance and difficulty of DNA pool construction.

TABLE 9

Pool ID and % T calculated values

| Pool ID | Pool Size (N) | % T |
|---|---|---|
| SNP465R:1 | 90 | 35.6 |
| SNP465R:2 | 71 | 33.7 |
| SNP465R:3 | 55 | 30.6 |
| SNP465R:4 | 39 | 25.0 |
| SNP461R:1 | 90 | 7.8 |

TABLE 9-continued

Pool ID and % T calculated values

| Pool ID | Pool Size (N) | % T |
|---|---|---|
| SNP461R:2 | 80 | 9.8 |
| SNP461R:3 | 67 | 12.8 |
| SNP461R:4 | 58 | 17.8 |

TABLE 10

Results for SNP456R and SNP461R

| Pool ID | % T | Std[%] | % T [95% Conf. Interval] | % T [99% Conf. Interval] |
|---|---|---|---|---|
| SNP465R:1 | 34.9 | 0.9 | 34.3–35.5 | 34.0–35.8 |
| SNP465R:2 | 31.6 | 1.4 | 30.6–32.6 | 30.2–33.0 |
| SNP465R:3 | 28.6 | 0.7 | 28.1–29.1 | 27.9–29.3 |
| SNP465R:4 | 27.3 | 1.4 | 26.3–28.3 | 25.9–28.7 |
| SNP461R:1 | 3.5 | 1.2 | 2.6–4.4 | 2.3–4.7 |
| SNP461R:2 | 6.1 | 0.9 | 5.5–6.7 | 5.2–7.0 |
| SNP461R:3 | 8.6 | 1.6 | 7.5–9.7 | 7.0–10.2 |
| SNP461R:4 | 15.4 | 1.3 | 14.5–16.3 | 14.1–16.7 |

EXAMPLE 5

Peak Height Linearity

To establish that a correlation exists between peak heights obtained in a primer-extension reaction, and the underlying allele frequency, 3 SNPs were investigated, Eu1, Eu4 and Eu7. The DNA samples were amplified according to Example 1. Following PCR amplification, 2 homozygote samples were mixed in proportions in 5% increments from 0% to 100% (i.e. 0:100, 5:95, . . . , 100:0). The primer-extension reaction was performed according to Example 3, and the allele frequencies calculated. 5 pmol PCR product was used for each primer-extension reaction, resulting in single peak height levels that were about 30–40 RLU (relative light units). The peak heights in RLU were plotted against the expected allele frequencies (FIGS. 4a, 4b and 4c). A linear relationship over the complete range of tested allele frequencies was confirmed. Thus, the correlation between primer-extension peak heights and SNP allele frequencies is excellent. FIG. 5 depicts the linear relationship between allele frequency and peak height, and shows the peak height results for 3 primer extension reactions: 25% C, 50% C and 75% C.

SNPs Present in Homopolymeric Stretches

To establish whether the presence of a homopolymeric stretch over an SNP alters the applicability of the method of the invention, primer-extension reactions were performed for 3 SNPs. Synthesized oligonucleotides (Interactiva, supra) were used in order to obtain an SNP where both alleles are located in a homopolymer, or where the SNP lies in a homopolymer of 3 or more identical residues.

Prior to all experiments, the DNA pools were calibrated using the method described in Example 2. For each SNP, 10 replicates of individual genotypes were analyzed in order to obtain reference data for comparison with the pools. The following SNPs were investigated:

1000F is a C/T-SNP which is preceded by a C. 24 samples were used to create five pools with different expected allele frequencies. (3,8% C, 7,1% C, 10% C, 31,2% C and 39,4% C). In the experiment, ten replicates were analyzed for each pool.

345F is an A/G-SNP followed by GGG. 24 samples were used to create two pools with an expected allele frequency of 26% A and 10% A respectively. Both pools were sequenced with two different dispensation orders to achieve either two or three peaks for the SNP. In the experiment, ten replicates were analyzed for each pool.

SNP471F is a C/T SNP preceded by CC. Eight samples were used to create four different pools with an expected allele frequency of 4.5% T, 8% T, 21% T and 31% T respectively. In the experiment, ten replicates were analyzed for each pool.

Oligo 1, Oligo 2 and Oligo 3 are artificially created SNPs that were made by mixing two oligonucleotides that only differ in one base. (See table 2). The two differing oligonucleotides were in each case mixed together with the following ratios: 5:95, 10:90, 20:80, 50:50, 80:20, 90:10 and 95:5. Oligo 1 is a C/T SNP preceded by CCC, Oligo 2 is a C/T SNP preceded by CCCC, and Oligo 3 is a C/T SNP preceded by CCCC and followed by TT.

Results

1. SNP 1000F. (CC/T)

Prior to the experiment this SNP was also used to calibrate the samples for the DNA pools. 30 µl of PCR product was incubated with 10 µl magnetic beads and 20 µl 2×BW-buffer. Pool 1 and Pool 2 show the difference in allele frequency between a calibrated pool (Pool 2) and a pool where the same volume of each sample has been used (Pool 1). Before the calibration, Pool 1 was expected to have an allele frequency of 31.2. This was based on the assumption that all samples were of the same DNA concentration. The calibration shows that this is not the case and based on the relative concentrations of the samples it is now possible to re-calculate the expected allele frequency of Pool 1 to be 39.4, which is much closer to the allele frequency that was obtained in the experiment. The results for these experiments are represented graphically as FIG. 6.

TABLE 11

The obtained allele frequencies for 1000F compared to the expected frequencies and the STD for each pool.

| Replicate | Pool 1 | Pool 2 | Pool 3 | Pool 4 | Pool 5 |
|---|---|---|---|---|---|
| 1 | 40.9 | 31.5 | 12.2 | 11.3 | 9.1 |
| 2 | 43.4 | 35.2 | 14.8 | 12.3 | 9.9 |
| 3 | 43.6 | 34.1 | 14.1 | 13.0 | 8.8 |
| 4 | 42.0 | 35.9 | 14.0 | 11.9 | 8.9 |
| 5 | 42.2 | 37.4 | 14.8 | 11.9 | 8.9 |
| 6 | 43.1 | 34.3 | 11.3 | 12.8 | 8.7 |
| 7 | 43.4 | 36.1 | 13.1 | 11.7 | 7.3 |
| 8 | 45.1 | 32.7 | 13.0 | 12.5 | 7.4 |
| 9 | 39.1 | 34.0 | 14.3 | 12.5 | 9.3 |
| 10 | 46.6 | 33.4 | 13.6 | 9.3 | 8.9 |
| average | 42.9 | 34.4 | 13.5 | 11.9 | 8.7 |
| expected | 39.4 | 34.2 | 10 | 7.1 | 3.8 |
| STD | 2 | 1.66 | 1.09 | 1 | 0.76 |

2. SNP 345F (A/GGGG).

30 µl of PCR product was incubated with 10 µl of magnetic beads and 20 µl of 2×BW-buffer. Two pools were made with the expected allele frequencies of 10% A and 26% A.

A comparison was made between a dispensation order (i.e. order of addition of nucleotides in the primer extension reaction) that generates two peaks and one that generates three peaks if the sample is a heterozygote. The small differences in allele frequency between the two different dispensation orders indicates that the result is not significantly influenced by whether the SNP has two or three informative peaks. The results are depicted graphically as FIGS. 8a and 8b.

In this SNP the A-peak reduction factor was set to 80% due to the higher peak obtained when using modified dATP (dATP S). This was based on calculations of allele frequencies in a run with individual samples. (The individual samples were run with a dispensation order that generates three peaks.) Despite with adjustment the SNP does not show a completely linear relationship between peak heights and allele frequency for individual samples. The obtained pool results are higher than expected, with the largest aberration in the lower frequencies. If the pool results are compared with the frequencies for 345F in individual samples (FIG. 7) one can see that the pattern is similar. However, it is difficult to do any allele frequency studies on a SNP that is not linear. The results for this SNP are depicted graphically as FIG. 7. The standard line shows an imaginary pattern for an "ideal" SNP.

TABLE 12

The obtained allele frequencies for 345 F. compared to the expected frequencies and the STD for each pool.

| Replicate | Pool 1 2 peaks | Pool 1 3 peaks | Pool 2 2 peaks | Pool 2 3 peaks |
|---|---|---|---|---|
| 1 | 36.0 | 35.7 | 14.5 | 15.5 |
| 2 | 35.8 | 33.7 | 17.2 | 17.2 |
| 3 | 34.5 | 34.6 | 13.6 | 16.3 |
| 4 | 36.6 | 35.2 | 15.2 | 15.8 |
| 5 | 33.2 | 32.9 | 11.4 | 12.4 |
| 6 | 34.1 | 35.1 | 12.2 | 13.9 |
| 7 | 33.7 | 35.0 | 12.7 | 15.4 |
| 8 | 32.8 | 35.5 | 12.5 | 16.1 |
| 9 | 35.7 | 31.2 | 14.4 | 16.8 |
| 10 | 34.0 | 33.7 | 13.6 | 15.6 |
| average | 34.6 | 34.3 | 13.7 | 15.5 |
| expected | 26 | 26 | 10 | 10 |
| STD | 1.23 | 1.33 | 1.6 | 1.35 |

3. SNP471F (CCC/T).

30 µl of PCR product was incubated with 101 µl of magnetic beads and 20 ul 2×BW-buffer. Four pools were made with the expanded allele frequencies of 68.7% C, 78.6% C, 91.7% C and 95.5% C.

TABLE 13

The obtained allele frequencies for SNP471F compared to the expected frequencies and the STD for each pool. The results are depicted graphically as FIG. 9. The standard line shows an imaginary pattern for an "ideal" SNP.

| Replicate | Pool 1 | Pool 2 | Pool 3 | Pool 4 |
|---|---|---|---|---|
| 1 | 64.0 | 76.6 | 87.6 | 93.1 |
| 2 | 61.2 | 73.3 | 86.1 | 91.7 |
| 3 | 62.3 | 76.9 | 86.0 | 92.0 |
| 4 | 66.0 | 76.7 | 86.7 | 91.0 |
| 5 | 65.3 | 79.8 | 85.5 | 91.9 |
| 6 | 57.5 | 77.3 | 86.3 | 90.0 |
| 7 | 68.6 | 79.3 | 85.6 | 90.1 |
| 8 | 68.0 | 78.2 | 84.3 | 92.0 |
| 9 | 70.5 | 74.5 | 88.2 | 90.7 |
| 10 | | | | 91.1 |
| average | 64.8 | 77.0 | 86.2 | 91.5 |
| expected | 68.7 | 78.6 | 91.7 | 95.5 |
| STD | 3.83 | 1.96 | 1.1 | 0.81 |

4. Oligo 1 (CCCC/T), Oligo 2 (CCCCC/T) and Oligo 3 (CCCCC/TTT).

The two oligonucleotides used for each artificial SNP were mixed in different ratios to a final concentration of 1 pmol/μl. 2 ul of each mix were annealed with 10 pmol of sequencing primer in a volume of 45 μl.

The obtained average allele frequencies for Oligo 1 and 2 (FIG. 10b) are within 10% from the expected frequencies although the results do not seem to be completely linear. Oligo 3 (FIG. 10c) shows that a SNP with two homopolymeric stretches can not be expected to give reliable allele frequencies; it is far from the expected frequencies. A cumulative representation of the results is shown as FIG. 10d.

EXAMPLE 6

Template Quantity

It is important to use the correct amount of nucleic acid in order to reliably estimate allele frequency. To investigate the amount of genomic DNA required prior to amplification, the SNP465R was investigated. 10 ng, 1 ng, 0.1 ng and 0.05 ng DNA was added in 4 PCR amplification and subsequent primer-extension reactions. Four DNA pools were created from genomic DNA, with allele frequencies of 31% C, 19% C, 12.5% C and 6% C. Standard calibration was performed 20 μl of PCR product was used in primer-extension.

Results

The experiment showed a significant correlation between the amount DNA used in the PCR reaction and the variation between replicates. In samples where 10 ng DNA were used in the PCR, the deviations between replicates were small but increased quickly when the template amount was lowered. But even for samples where only 0.05 ng DNA were used, the average allele frequencies of 10 replicates were in good accordance with the expected. A template amount of at least 10 ng is required for a reliable allele frequency quantification if only one or few replicates are used. If many replicates are amplified, the average allele frequency will be correct even with lower DNA amount but the variation between replicates will be significant. The results are depicted graphically on FIGS. 11a, b, c and d.

Required Signal Level

The height of the peak measured during primer-extension is correlated to many factors, including the amount of PCR product used. In order to determine the threshold signal level to calculate allele frequencies, several experiments were performed. Four different SNPs with different expected allele frequencies were used. One C/A-SNP (470R), one T/G-SNP (481R), one T/C-SNP with a T before the SNP (486R) and one C/T-SNP with a C before the SNP (460R). For SNP 470, a pool was created of several genomic samples. The expected allele frequency was 55% A in this pool. For the other SNPs a different pool of samples was used. The expected allele frequencies in that pool was 19.5% G for SNP481R, 12.5% C for SNP486R and 6% G for SNP460R.

Results

The peak heights do not seem to affect the allele frequency results in any dramatic way. If the single peak height is below 10 RLU, the signal-to-noise ratio might be too low for the SNP, if one of the alleles is represented at a low frequency. Although quite small, the variation between replicate reactions seems to increase slightly when the average single-peak height level gets below 15 RLU. The results are represented graphically as figure (12).

All references cited herein are incorporated herein in their entirety.

The invention claimed is:

1. A method of determining the frequency of an allele in a population of nucleic acid molecules, said method comprising:

pooling the nucleic acid molecules of said population to provide a pooled nucleic acid sample; performing primer extension reactions in a reaction mixture comprising said pooled nucleic acid sample and a primer which binds at a predetermined site located in said nucleic acid molecules, wherein said site is substantially adjacent to a polymorphic position of interest in said allele, to provide primer extension products, and wherein the primer extension reaction is performed by sequentially adding non-chain terminating nucleotides to the reaction mixture and quantitatively determining the incorporation or non-incorporation of each nucleotide as each nucleotide is added by bioluminometrically detecting the release of pyrophosphate; obtaining a pattern of nucleotide incorporation in said primer extension products at the positions that correspond to said polymorphic position of interest; and determining the frequency of said allele from said pattern of nucleotide incorporation.

2. The method according to claim 1 wherein ELIDA detection enzymes are used to detect the release of pyrophosphate.

3. The method according to claim 2 wherein a nucleotide-degrading enzyme is included during the primer extension reaction.

4. The method according to claim 1 wherein the nucleic acid molecules are immobilized on a solid support.

5. The method according to claim 1 wherein the amount or concentration of the nucleic acid in each sample of the population which is pooled, is determined prior to pooling.

6. The method according to claim 5 wherein the concentration of the nucleic acid in each sample of the population is determined by a primer-extension reaction prior to pooling.

7. The method according to claim 6 wherein the volume of each nucleic acid in each sample to be pooled is adjusted in view of the amount or concentration of nucleic acid present such that the pooled sample contains substantially the same amount or concentration of each nucleic acid molecule in the population.

8. The method according to claim 7 wherein a particular polymorphism is selected as a reference polymorphism and said primer extension reaction used to determine the concentration of nucleic acid in said sample is specific for said reference polymorphism.

9. The method according to claim 8 wherein said polymorphism is chosen such that it gives no background signals in a primer-extension reaction and that the signals are even.

10. The method according to claim 8 wherein said polymorphism is not present in a homopolymeric sequence and will not be preferentially amplified in any PCR-type reactions.

11. The method according to claim 8 wherein a reference sample containing said polymorphism is selected as the main reference from one of the homozygotes of one of the alleles of said polymorphism (Ref 1) and another reference (Ref 2) containing said polymorphism is selected from the other homozygote, and the reference samples are pooled and primer extension reactions are performed, and the pattern of nucleotide incorporation determined to determine the relative concentration of each reference sample.

12. The method according to claim 11 wherein the sample nucleic acid molecules to be tested are pooled individually with the reference samples.

13. A method of determining the amount of an allele in a sample of nucleic acid molecules, said method comprising:

performing primer extension reactions in a reaction mixture comprising said nucleic acid molecules, using a primer which binds at a predetermined site located in at least one said molecule wherein said site is substantially adjacent to a polymorphic position of interest in said allele, to provide primer extension products, and wherein the primer extension reaction is performed by sequentially adding non-chain terminating nucleotides to the reaction mixture and quantitatively determining the incorporation or non-incorporation of each nucleotide as each nucleotide is added by bioluminometrically detecting the release of pyrophosphate; determining the type and number of nucleotides incorporated in said primer extension products at positions that correspond to the polymorphic position of interest, and determining the amount of occurrence of said allele in said sample by analyzing the type and number of nucleotides incorporated.

14. The method according to claim 13 wherein ELIDA detection enzymes are used to detect the release of pyrophosphate.

15. The method according to claim 14 wherein a nucleotide-degrading enzyme is included during the primer extension reaction.

16. The method according to claim 15 wherein the nucleic acid molecules are immobilized on a solid support.

* * * * *